United States Patent
Matsushige et al.

(10) Patent No.: US 8,357,731 B2
(45) Date of Patent: *Jan. 22, 2013

(54) ONE-PACKAGE TYPE TOOTH SURFACE COATING MATERIAL

(75) Inventors: Koji Matsushige, Tsukuba (JP); Qian Cui, Moriya (JP); Mikio Kimura, Joso (JP)

(73) Assignee: Tokuyama Dental Corporation, Tokyo (JP)

( * ) Notice: Subject to any disclaimer, the term of this patent is extended or adjusted under 35 U.S.C. 154(b) by 254 days.

This patent is subject to a terminal disclaimer.

(21) Appl. No.: 12/738,473

(22) PCT Filed: Oct. 8, 2008

(86) PCT No.: PCT/JP2008/068274
§ 371 (c)(1),
(2), (4) Date: Apr. 16, 2010

(87) PCT Pub. No.: WO2009/051045
PCT Pub. Date: Apr. 23, 2009

(65) Prior Publication Data
US 2010/0216907 A1 Aug. 26, 2010

(30) Foreign Application Priority Data
Oct. 16, 2007 (JP) .................. 2007-268873

(51) Int. Cl.
*A61K 6/08* (2006.01)
*C08K 3/22* (2006.01)
*C08K 3/36* (2006.01)

(52) U.S. Cl. .............. 522/79; 522/81; 522/84; 522/171; 523/115; 523/118

(58) Field of Classification Search .................. 523/115, 523/118, 120; 522/79, 84, 81, 171
See application file for complete search history.

(56) References Cited

U.S. PATENT DOCUMENTS
5,744,511 A * 4/1998 Kazama et al. ................ 522/25
(Continued)

FOREIGN PATENT DOCUMENTS
JP 6-256131 A 9/1994
(Continued)

OTHER PUBLICATIONS
International Search Report (PCT/ISA/210) dated Nov. 11, 2008.

*Primary Examiner* — Susan W Berman
(74) *Attorney, Agent, or Firm* — Buchanan Ingersoll & Rooney PC

(57) ABSTRACT

A one-package type tooth surface coating material that is capable of forming, on the surface of a tooth, a cured film having not only a very high strength of adhesion to the tooth surface but also excellent properties such as long-term adhesion, long-term durability, dentinal tubule occlusion and aesthetic appearance, and that has excellent storage stability and can be stored in the form of one package. The one-package type tooth surface coating material includes (A) a polymerizable monomer component containing not less than 5% by mass of an acidic group-containing polymerizable monomer; (B) polyvalent metal ions; (C) a volatile water-soluble organic solvent; (D) water; and (E) an effective amount of a photopolymerization initiator; the amount of the polyvalent metal ions (B) and the amount of the volatile water-soluble organic solvent (C) satisfying a specific relationship.

5 Claims, 2 Drawing Sheets

U.S. PATENT DOCUMENTS

| | | |
|---|---|---|
| 6,191,190 B1 * | 2/2001 | Blackwell et al. ............ 523/115 |
| 6,583,197 B1 * | 6/2003 | Wada et al. .................... 522/84 |
| 2009/0075189 A1 * | 3/2009 | Hung et al. .................... 430/20 |
| 2009/0076189 A1 * | 3/2009 | Matsushige et al. .......... 523/120 |
| 2010/0261144 A1 * | 10/2010 | Fujinami et al. ........... 433/228.1 |

FOREIGN PATENT DOCUMENTS

| | | |
|---|---|---|
| JP | 10-236912 A | 9/1998 |
| JP | 10-245525 A | 9/1998 |
| JP | 11-130465 A | 5/1999 |
| JP | 2002-226314 A | 8/2002 |
| WO | WO 2007/139207 A1 | 12/2007 |

* cited by examiner

ONE-PACKAGE TYPE TOOTH SURFACE COATING MATERIAL

TECHNICAL FIELD

This invention relates to a tooth surface coating material used in the field of dental therapy and, more particularly, to a one-package type dental surface coating material which can be stored as one package and can be used for forming an outer coating directly on the surfaces of teeth.

BACKGROUND ART

A tooth surface coating material comprising a curable composition has heretofore been used for various purposes in the dental field. To prevent decaying or to suppress hypersensitivity, for instance, a tooth surface coating material is applied to a predetermined portion on the tooth surface and is cured to form a cured film. That is, upon coating a predetermined portion on the tooth surface with the cured film of the tooth surface coating material, the decaying can be prevented and, besides, hypersensitivity such as smarting of a tooth can be suppressed. The tooth surface coating material is, further, used as an opaquer for shielding the discoloration of the tooth surface and as a dental manicure for improving aesthetic appearance of the tooth surfaces.

The tooth surface coating material is different from the dental adhesives that adhere and fix a composite resin or a prosthetic material to the tooth with respect to that the tooth surface coating material forms by itself the cured film which serves as the outer surface coating that is exposed directly on the surface of the tooth. The tooth surface coating material, however, shares the requirement of adhesion to the tooth with the dental adhesive. Therefore, though not so many proposals have heretofore been made as tooth surface coating materials, many adhesives have now been proposed having good adhesiveness to the teeth, and it has now been considered that the adhesives can also be applied as coating materials for the tooth surfaces (e.g., patent documents 1 and 2).

Many of the dental curing compositions used as adhesives contain (meth)acrylic acid esters as polymerizable monomers and, therefore, have been blended with photopolymerization initiators without, however, capable of exhibiting a sufficient degree of adhesion to the teeth. Therefore, it has been desired to improve their adhesiveness to the teeth.

In order to effectively improve the adhesiveness of the adhesive to the teeth, it is an accepted practice to pre-treat the tooth in two steps as described below prior to applying the adhesive to the teeth.
(1) Apply an aqueous solution (etching agent) of an acid such as phosphoric acid, citric acid or maleic acid to the surface of the tooth, and etch the hard tooth (mainly enamel).
(2) After the etching, a solution (permeation accelerator or also called primer) containing an amphiphilic monomer such as hydroxyethyl methacrylate (HEMA) or the like and an organic solvent as chief components is applied so that the permeation accelerator permeates into the tooth (dentin).

However, these pre-treatments require complex operations. Therefore, there has been developed an adhesive which is imparted with a function (primer function) equivalent to that of the pre-treatment. For example, a patent document 3 is proposing a dental adhesive containing a polymerizable monomer (acidic group-containing polymerizable monomer) that contains an acidic group such as phosphoric acid group or carboxylic acid group as part of the polymerizable monomer and, further, containing a predetermined amount of water and a photopolymerization initiator. The acidic group-containing polymerizable monomer in this adhesive exhibits tooth deliming property and affinity to dentin. Besides, water contained therein works to effectively conduct the tooth deliming. It is, therefore, allowed to form a cured product that strongly adheres to both the enamel and the dentin in the initial stage of adhesion through a simple operation without the need of conducting the above-mentioned pre-treatment.

The patent document 3, further, proposes blending a polyvalent metal ion-eluting filler (e.g., fluoroaluminosilicate glass) making it possible to further improve the adhesion to the teeth. That is, the dental adhesive has the above-mentioned primer function (deliming function for the teeth and permeation acceleration function for the dentin) and, further, develops ionic crosslinking at the time of curing owing to the interaction among the acidic group-containing polymerizable monomer, water and polyvalent metal ions eluted out from the filler in addition to the radical polymerization of the polymerizable monomer. Owing to the synergistic action of these radical polymerization and ionic crosslinking, there is formed a cured product that strongly adheres to both the enamel and the dentin.

Patent document 1: JP-A-06-256131
Patent document 2: JP-A-10-245525
Patent document 3: JP-A-10-236912

DISCLOSURE OF THE INVENTION

Problems that the Invention is to Solve

The tooth surface coating material by itself forms a cured film that serves as an outer surface coating, the cured film realizing the prevention of decaying and suppression of hypersensitivity. It is, therefore, required that the tooth surface coating material maintains a strong adhesion to the teeth for extended periods of time (long-term adhesion) and must maintain excellent abrasion resistance and a predetermined film thickness for extended periods of time (long-term durability). From the standpoint of suppressing hypersensitivity, in particular, it is required that when applied onto the exposed surfaces of the dentin, the tooth surface coating material must permeate deep into the dentinal tubules and is cured therein (dentinal tubule occlusion) to prevent external stimuli from being transmitted to the nerve cells in the dental pulp through the dentinal tubules. Aesthetic appearance is, further, required for not to impair the appearance of the tooth surface. When the coating material is used as a dental manicure, in particular, the aesthetic appearance becomes the most important factor. When used as the dental surface coating material, however, the above-mentioned dental adhesives all fail to satisfy properties specifically required for the dental surface coating material, such as long-term adhesion, long-term durability, dentinal tubule occlusion and aesthetic appearance.

With the dental adhesive (photocurable composition) containing an acidic group-containing polymerizable monomer, for example, the acidic group-containing polymerizable monomer is a relatively highly hydrophilic monomer and, therefore, the obtained cured body has a low water-resisting property and cannot maintain a long-term adhesion to a sufficient degree when used as the tooth surface coating material. When used as the tooth surface coating material, the cured film thereof must stay in the oral cavity for extended periods of time in a state where it is directly exposed to a severe environment containing much water. If the water-resisting property is low, therefore, the adhering force of the cured film to the tooth surface decreases with the passage of time. Besides, since the acidic group-containing polymerizable monomer is hydrophilic, the cured film thereof easily absorbs water. As a result, the cured film is subject to be abraded due to brushing the teeth, failing to maintain a long-term durability, permitting the surface of the cured film to become cloudy, and losing luster on the surface of the cured film. Therefore, the tooth surface coating material requires improvements even from the standpoint of maintaining aesthetic appearance.

Moreover, when the above dental adhesive is used as the dental coating material, the requirement of dentinal tubule occlusion is not satisfied, either. That is, the above dental adhesive has excellent primer functions such as tooth deliming property and permeability into dentin and, therefore, permeates deep into the dentinal tubules when it is applied onto the exposed surface of the dentin. When it is attempted to cure the dental adhesive deep in the dentinal tubules, however, light that is projected reaches the coating material little which, therefore, is not effectively polymerized or cured in the dentinal tubules. Therefore, even if the cured film is formed on the surface of the dentin, the strength of adhesion is not satisfactory and, besides, the dentinal tubule occlusion is not satisfactory, either.

Moreover, the photocurable composition of the patent document 3 has a problem from the standpoint of storage stability.

That is, gelation easily takes place if the polyvalent ion-eluting filler is stored in the form of one package being mixed with the acidic group-containing polymerizable monomer and other components. Therefore, the above photocurable composition had to be stored in the form of two packages being divided into two liquids, i.e., a liquid containing the acidic group-containing polymerizable monomer and a liquid containing the polyvalent ion-eluting filler. When stored in the form of two packages, the two liquids must be mixed together at a clinic just before a dentist is going to use them, involving very cumbersome work for the dentist and inevitably accompanied by some degree of dispersion in the mixing conditions, such as mixing operation and mixing time depending upon the individual operators leaving problems such as requiring a skill.

It is, therefore, an object of the present invention to provide a one-package type tooth surface coating material that is capable of forming, on the surface of a tooth, a cured film having not only a very high strength of adhesion to the tooth surface but also excellent properties such as long-term adhesion, long-term durability, dentinal tubule occlusion and aesthetic appearance, and that has excellent storage stability and can be stored in the form of one package.

Means for Solving the Problems

In order to solve the above technical problems, the present inventors have conducted keen study, have discovered the fact that a curable composition obtained by blending a polymerizable monomer that contains an acidic group-containing polymerizable monomer, polyvalent metal ions, water, a volatile water-soluble organic solvent and a photopolymerization initiator so as to satisfy specific conditions, can be used as a one-package type tooth surface coating material featuring excellent storage stability and is capable of forming a cured film that exhibits the above mentioned properties, and have thus completed the invention.

According to the present invention, there is provided a one-package type tooth surface coating material that can be stored as one package and can be used for forming an outer surface coating directly on the surface of a tooth, comprising:

(A) a polymerizable monomer component containing not less than 5% by mass of an acidic group-containing polymerizable monomer;
(B) polyvalent metal ions;
(C) a volatile water-soluble organic solvent;
(D) water; and
(E) an effective amount of a photopolymerization initiator;

the polyvalent metal ions (B) being present in an amount of 1.0 to 7.0 meq per gram of the polymerizable monomer component (A);

the water-soluble organic solvent (C) being blended in an amount in a range of 30 to 150 parts by mass per 100 parts by mass of the polymerizable monomer component (A) and satisfying a condition represented by the following formula (I), $$\alpha \geqq 20 \cdot X \tag{I}$$

wherein α is a blended amount of the water-soluble organic solvent (C) per 100 parts by mass of the polymerizable monomer component (A), and X is the amount of the polyvalent metal ions and is a number representing the amount (meq) thereof per gram of the polymerizable monomer component (A), and the water (D) being blended in an amount of 3 to 30 parts by mass per 100 parts by mass of the polymerizable monomer component (A).

In the one-package type tooth surface coating material as described in claim 1 of the present invention, it is desired that:
(1) The polyvalent metal ions (B) are present being eluted out from a polyvalent metal ion-eluting filler;
(2) A coloring agent (F) is, further, contained;
(3) The acidic group-containing polymerizable monomer in the polymerizable monomer component (A) is a polymerizable monomer containing a phosphoric acid group; and
(4) The polyvalent metal ion-eluting filler permits the polyvalent metal ions to be eluted out in an amount of 5.0 to 500 meq/g of filler when 0.1 g of the filler is added to 10 ml of an aqueous solution containing 10% by weight of maleic acid and is maintained therein at 23° C. for 24 hours.

Effects of the Invention

The tooth surface coating material of the invention is applied to a predetermined portion on the tooth surface and, thereafter, the air, for example, is blown thereto to volatilize the volatile water-soluble organic solvent (C), followed by the irradiation with light to polymerize and cure the coating material to thereby form a cured film that serves as an outer surface coating directly on the surface of the tooth.

When the components in the tooth surface coating material of the invention are applied to the tooth surface, the acidic group-containing polymerizable monomer contained in the polymerizable monomer component (A) exhibits a primer function (tooth deliming function and permeation into the dentin) to a sufficient degree and, besides, a polymer chain is ionically crosslinked due to the interaction of the acidic group-containing polymerizable monomer (A), polyvalent metal ions (B) and water (C) in addition to the polymerization and curing of the polymerizable monomer component (A). Further, the curing by polymerization and the ionic crosslinking synergistically act to each other, making it possible to form a cured film that strongly adheres to both the enamel and the dentin.

As is demonstrated in Examples appearing later, the cured film has a high water-resisting property, strongly adheres to the tooth surface (enamel and dentin) for extended periods of time, maintains luster on the tooth surface for extended periods of time, and is also excellent from the standpoint of aesthetic appearance. The cured film, further, has excellent abrasion resistance, and is greatly suppressed from being abraded even when the teeth are brushed many times repetitively; i.e., the cured film has very excellent durability.

Further, the surface coating material of the invention has a remarkable feature in that the composition thereof is suitably adjusted with the water-soluble organic solvent (C) so that the amount of the polyvalent metal ions (B) becomes a predetermined amount lying in a suitable range of concentration. When stored, therefore, the gelation due to the ionic crosslinking is suppressed down to a level free of problems, and the surface coating material can be stored as one package. Besides, the water-soluble organic solvent (C) used for adjusting the concentration of the polyvalent metal ions is volatile and can, therefore, be easily volatilized by blowing the air thereto after it has been applied. That is, the polyvalent metal ions can be concentrated within a short period of time so as to attain a strong ionic crosslinking. As a result, adhesion due to the polymerization and curing of the monomer component and the adhesion due to ionic crosslinking of the polymer of the acidic group-containing polymerizable monomer are attained without almost impaired creating a synergistic effect and, therefore, a highly strong adhesion is secured for both the enamel and the dentin as described above.

Further, as demonstrated in Examples appearing later, the cured film formed by using the tooth surface coating material of the invention exhibits very excellent dentinal tubule occlusion.

FIG. 2, for example, is an SEM photograph showing the surface of a model of hypersensitive dentin used for testing the dentinal tubule occlusion. As will be learned from FIG. 2, ends of a number of dentinal tubules are present in an open state in the exposed surface of the dentin. That is, if the dentin of a tooth is exposed due to decaying, external stimuli are transmitted to the nerve cells in the dental pulp through dentinal tubules triggering hypersensitivity such as smarting of a tooth.

The tooth surface coating material of the invention, however, permeates deep into the dentinal tubules and is effectively cured even in the portions that have deeply permeated exhibiting very excellent dentinal tubule occlusion and effectively suppressing hypersensitivity. FIG. 3, for example, is an SEM photograph of a cross section of when the tooth surface coating material of the invention is applied onto the surface of the above model of hypersensitive dentin, polymerized and cured by the irradiation with light, treated with an acid to dissolve and remove the surface portions of the dentin of the model, and when the dentin is vertically cut. A number of tags observed in FIG. 3 are the portions that have permeated into the dentinal tubules and are cured therein. It will, therefore, be learned that the tooth surface coating material permeates deep into the dentinal tubes and is effectively cured.

Though the reason has not been clarified yet why the tooth surface coating material of the invention exhibits excellent dentinal tubule occlusion as described above, the present inventors speculate it as described below.

That is, the tooth surface coating material of the invention contains the acidic group-containing polymerizable monomer and exhibits excellent primer function, favorable storage stability, and effectively suppresses gelation. Therefore, the tooth surface coating material permeates deep into the dentinal tubules. Besides, the organic solvent is removed upon being blown with the air, the concentration of polyvalent metal ions is heightened to form the ionic crosslinking to a sufficient degree, and the polymerization and curing are conducted by the irradiation with light in a state where the viscosity has sharply increased. As a result, it is considered that the polymerization efficiency is greatly enhanced due to an increased viscosity, and the coating agent is very strongly solidified to form a cured product even deep in the dentinal tubules, and excellent dentinal tubule occlusion is obtained.

The tooth surface coating material of the invention having the above properties is used for such purposes as preventing oral diseases and improving aesthetic appearance of the teeth, and is used, for example, as an opaquer for shielding discoloration on the tooth surface, a dental manicure, or as a coating material for preventing decaying or for suppressing hypersensitivity. Depending upon the purposes, therefore, the dental coating material may be applied to the whole surface of the tooth to form a cured film that serves as an outer coating, or may be applied onto a portion only on the surface of the tooth to form the outer surface coating.

BEST MODE FOR CARRYING OUT THE INVENTION

Figure 1:
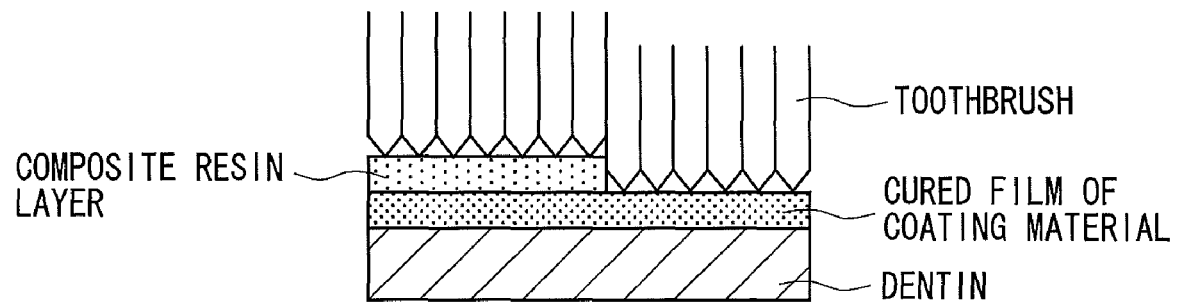
FIG. 1 is a view schematically illustrating a test piece used for testing the abrasion by using a tooth brush.

The one-package type tooth surface coating material of the invention comprises, as basic components, (A) a polymerizable monomer component, (B) polyvalent metal ions, (C) a volatile water-soluble organic solvent, (D) water, and (E) a photopolymerization initiator, and, depending upon the use, is further, blended with (F) a coloring agent, and is stored in the form of one package. The coating material can be, further, blended with a storage stabilizer and various blending agents that have been known in the dental field of art within ranges in which they do not impair properties of the cured film.

<Polymerizable Monomer Component (A)>

In the present invention, the polymerizable monomer component (A) (hereinafter simply referred to as "monomer component") is a component used for imparting adhesiveness to the tooth surface upon being polymerized and cured. In order to express etching ability (tooth deliming property) for the tooth and permeability into the dentin, however, at least not less than 5% by mass of the polymerizable monomer component (A) must be an acidic group-containing polymer (A1). That is, if the amount of the acidic group-containing polymer (A1) is small, the tooth surface coating material fails to exhibit a sufficient degree of etching ability to the tooth. To secure a sufficiently high strength of adhesion to the tooth, therefore, it becomes necessary to pre-treat the tooth.

The monomer component (A) may all be the acidic group-containing polymer (A1). To adjust the strength of the interface of adhesion, to adjust permeability into the tooth, to obtain excellently strong adhesion to the tooth and water-resisting property, and to adjust balance between hydrophilic property and hydrophobic property required for the tooth surface coating material, however, it is desired that the tooth surface coating material, further, contains a polymerizable monomer (A2) that does not contain acidic group.

For example, it is desired that the monomer component (A) contains the acidic group-containing polymer (A1) in an amount in a range of 5 to 50% by mass and, particularly, 10 to 30% by mass, and the remainder thereof is the polymerizable monomer (A2) without containing acidic group. Here, if the amount of the acidic group-containing polymerizable monomer (A1) is small, the strength of adhesion to the enamel tends to decrease. If the amount thereof is large, on the other hand, the strength of adhesion to the dentin tends to decrease.

Acidic Group-Containing Polymerizable Monomers (A1):

In the present invention, the acidic group-containing polymerizable monomer (A1) may be any known compound without particular limitation provided it has at least one acidic group and at least one polymerizable unsaturated group in the molecules thereof.

Described below are examples of the acidic group which the monomer (A1) has in the molecules thereof.

Acidic Groups:

[Chemical 1]

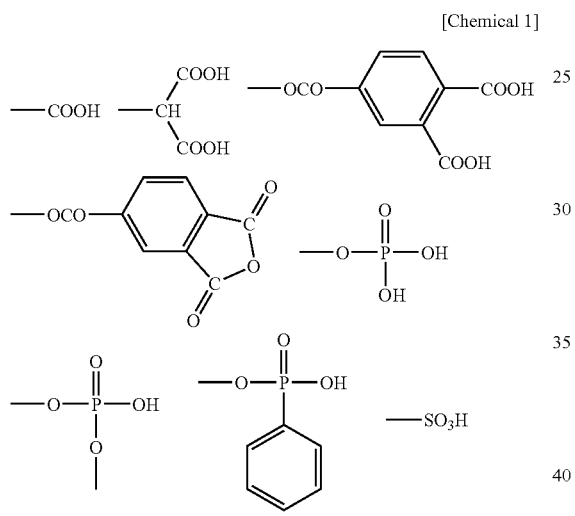

As the polymerizable unsaturated group which the monomer (A1) has in the molecules thereof, further, there can be exemplified acryloyl group, methacryloyl group, acrylamide group, methacrylamide group, vinyl group, allyl group, ethenyl group and styryl group.

In the invention, the compounds expressed by the following examples are concrete and representative examples of the polymerizable monomer (A1) that has the above acidic group and polymerizable unsaturated group in the molecules thereof.

Representative examples of the acidic group-containing polymer (A1):

[Chemical 2]

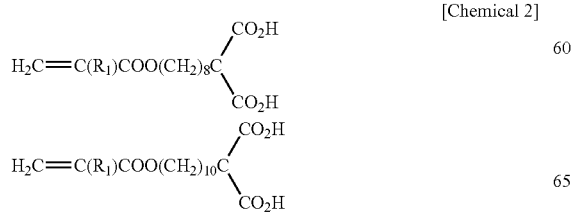

-continued

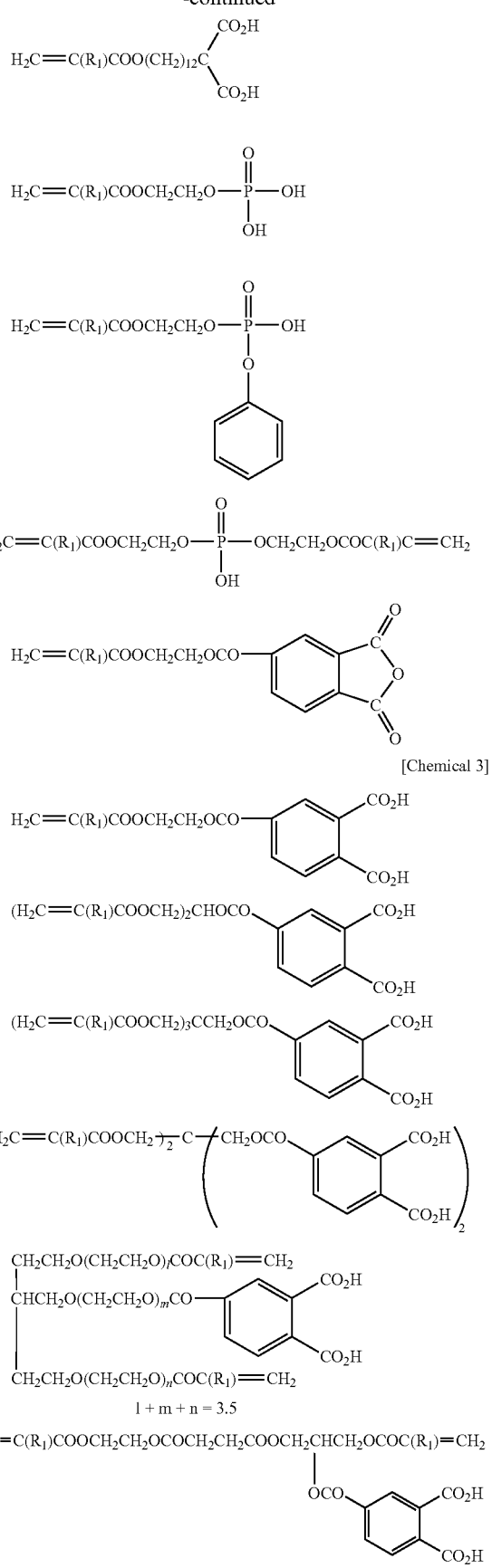

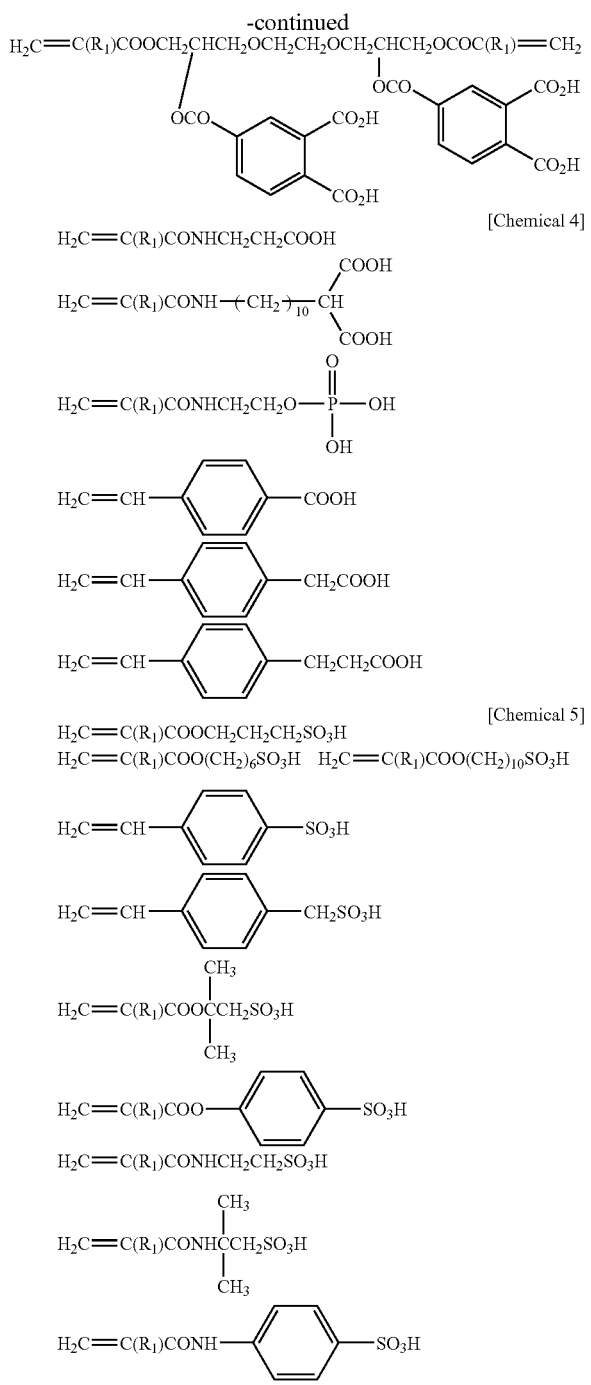

[Chemical 4]

[Chemical 5]

(wherein R[1] is a hydrogen atom or a methyl group).

In addition to the above compounds, there can be, further, used vinylphosphonic acids in which a phosphonic acid group is directly bonded to a vinyl group, acrylic acid, methacrylic acid or vinylsulfonic acid as the acidic group-containing polymer (A1).

The above acidic group-containing polymers (A1) can be used alone or being mixed in two or more kinds. Among them, it is desired to use a compound (polybasic acid compound) having an acid valency of two or more in the molecules from the standpoint of enhancing the ionic bond to the polyvalent metal ions (B) described later and obtaining a strong adhesion. The polybasic acid compound may have two or more monovalent acid groups in a molecule, or may have at least one acid group having a valency of two or more in a molecule. Use of the polybasic acid compound only as the acidic group-containing polymerizable monomer (A1) may be desirable from the standpoint of improving the strength decreasing, however, the storage stability in the one-package form tends to some degree. More desirably, therefore, the polybasic acid compound and the acidic compound having a monovalent acid in the molecule are used in combination from the standpoint of attaining both the strength of adhesion and the storage stability. The blending ratio, i.e., the polybasic acid compound:acidic compound having a monovalent acid in the molecule, is 1 to 5:1 and, more preferably, 1 to 3:1

When the polybasic acid compound and the monovalent acidic compound are used in combination as the acidic group-containing polymerizable monomer (A1) as described above, it is most desired that either compound contains a phosphoric acid type acid group (concretely, —O—P(=O) $(OH)_2$, $(—O—)_2P(=O)OH$, etc.) as the acidic group. In a system using the acidic group-containing polymerizable monomers (A1) of the above combination, there are obtained not only a high deliming action for the tooth (presumably, due chiefly to an acidic group of the phosphoric acid type having a strong acidity) but also a substantially high bonding strength to the tooth and, particularly, a high strength of adhesion, making it possible to obtain a favorable storage stability in the one-package form.

From the standpoint of curing rate, further, it is desired that the acidic group-containing polymerizable monomer (A1) is a compound having acryloyl group, methacryloyl group, acrylamide group or methacrylamide group as a polymerizable unsaturated group.

Polymerizable Monomers without Acidic Group (A2):

As the polymerizable monomer (A2) used in combination with the monomer (A1) but without having acidic group, there can be used any known compound without limitation provided it satisfies the conditions of not having acidic group but having at least one polymerizable unsaturated group in the molecule. As the polymerizable unsaturated group possessed by the above polymerizable monomer, there can be exemplified those groups exemplified concerning the above monomer (A1) and, particularly preferably, there can be exemplified acryloyl group, methacryloyl group, acrylamide group and methacrylamide group.

As representative examples of the polymerizable monomers (A2), there can be described the following (meth)acrylate type monomers which may be used in a single kind or in a combination of two or more kinds.

1. Mono(meth)acrylate Type Monomers:
methyl(meth)acrylate,
ethyl(meth)acrylate,
glycidyl(meth)acrylate,
2-cyanomethyl(meth)acrylate,
benzyl(meth)acrylate,
polyethylene glycol mono(meth)acrylate,
allyl(meth)acrylate,
2-hydroxyethyl(meth)acrylate,
3-hydroxypropyl(meth)acrylate,
glycerylmono(meth)acrylate,
2-(meth)acryloxyethylacetyl acetate, etc.

2. Polyfunctional (meth)acrylate Type Monomers:
ethylene glycol di(meth)acrylate,
diethylene glycol di(meth)acrylate,
triethylene glycol di(meth)acrylate,
nonaethylene glycol di(meth)acrylate,
propylene glycol di(meth)acrylate,
dipropylene glycol di(meth)acrylate, 2,2'-bis[4-(meth)acryloyloxyethoxyphenyl]propane,
2,2'-bis[4-(meth)acryloyloxyethoxyethoxyphenyl]propane,
2,2'-bis{4-[3-(meth)acryloyloxy-2-hydroxypropoxy]
   phenyl}propane,
1,4-butanedioldi(meth)acrylate,
1,6-hexanedioldi(meth)acrylate,
trimethylolpropanetri(meth)acrylate,
urethane(meth)acrylate,
epoxy(meth)acrylate, etc.

It is, further, allowable to use a polymerizable monomer other than the above (meth)acrylate type monomer being mixed thereto. As the other polymerizable monomer, there can be exemplified fumaric acid ester compounds such as monomethyl fumarate, diethyl fumarate and diphenyl fumarate; styrene compounds such as styrene, divinylbenzene, α-methylstyrene and α-methylstyrene dimer; and allyl compounds such as diallyl phthalate, diallyl terephthalate, diallyl carbonate and allyl diglycol carbonate. These other polymerizable monomers can be used in one kind or in two or more kinds being mixed together.

In the invention, further, when a highly hydrophobic polymerizable monomer is used as the polymerizable monomer (A2), it is desired to use in combination an amphiphilic monomer such as 2-hydroxyethyl(meth)acrylate or 2-hydroxypropyl(meth)acrylate. This is because use of the amphiphilic monomer in combination makes it possible to prevent isolation of water which is an essential component of the tooth surface coating material of the invention, to maintain homogeneity of the composition, to obtain stable and high strength of adhesion and, further, to realize excellent luster on the surface of the coating. The amphiphilic monomer is blended in an amount of 10 to 60% by mass and, more preferably, 30 to 45% by mass in the polymerizable monomer (A2).

<Polyvalent Metal Ions (B)>

It is important that the tooth surface coating material of the invention contains polyvalent metal ions as the component (B). The polyvalent metal ions work to introduce ionic crosslinking into the acidic group-containing polymerizable monomer (A1) (or a polymer thereof) making it possible to obtain a high strength of adhesion of the cured film to the tooth (enamel and dentin) due to synergistic effect of the ionic crosslinking and the curing by polymerization, to secure film properties such as water-resisting property and abrasion resistance, to secure a high strength of adhesion for extended periods of time, to maintain excellent durability and surface luster (aesthetic appearance) for extended periods of time and to enhance the dentinal tubule occlusion.

The polyvalent metal ions are metal ions having a valency of two or more and are capable of being bonded to an acidic group possessed by the polymerizable monomer (A1), and any polyvalent ions may be used so far as they are capable of being bonded to the acidic groups. From the standpoint of dental use, however, it is desired to use ions of calcium, strontium, barium, aluminum, scandium, ytterbium, titanium, zinc, magnesium, zirconium, vanadium, chromium, manganese, iron, cobalt, nickel, copper or lanthanoide. Among them, it is desired to use ions having a valency of three or more from the standpoint of high strength of adhesion and, most desirably, to use aluminum ions, lanthanum ions or titanium ions as the component from the standpoint of safety to the living body in addition to the high strength of adhesion.

It is important that the amount of the polyvalent metal ions (B) present in the tooth surface coating material of the invention is so adjusted as to be 1.0 to 7.0 meq and, particularly, 1.5 to 6.8 meq per gram of the above-mentioned monomer component (A). That is, upon adjusting the amount of the polyvalent metal ions per gram of the monomer component (A) to lie in the above range, it is allowed to form a cured film that strongly adheres onto the tooth surface due to a suitable degree of ionic crosslinking. If the amount of the metal ions is smaller than the above range, the ionic crosslinking becomes insufficient, and the strength of adhesion to the tooth decreases. If the amount thereof is larger than the above range, the tooth deliming power based on the acidic group-containing polymer (A1) decreases, and the volatile water-soluble organic solvent (C) is required in increased amounts for maintaining storage stability in the one-package form. When the tooth surface coating material is applied onto the tooth surface and is blown with the air to form a cured film, further, the polymerizable monomer component becomes insufficient. In either case, therefore, the strength of adhesion decreases.

In the present invention, the amount of polyvalent metal ions present in the tooth surface coating material is found by measuring the concentrations of various kinds of ions relying on the ICP emission spectroscopy or the atomic absorption spectroscopy, and by converting the amount of ionic bond of the polyvalent metal ions to the monomer component (A) obtained from the measured values into a milliequivalent per gram of the monomer component (A). Namely, the amount of polyvalent metal ions present in the tooth surface coating material can be found as a sum of values obtained by multiplying the concentrations of polyvalent metal ions (mmols/g) per gram of the monomer component (A) by the valencies of the respective metal ions.

As the source of ions for making present the polyvalent metal ions (B) in the above amount in the present invention, there can be used an ionic compound such as an alkoxide, a water-soluble salt, a water-soluble hydroxide, a water-soluble oxide or a complex salt of the above-mentioned polyvalent metal in amounts depending upon the degree of solubility or dissociation thereof. Concrete examples of the source of the polyvalent metal are as described below though not limited thereto only.

Alkoxides of Polyvalent Metals:
   aluminum triisopropoxide,
   magnesium hydroxide,
   calcium hydroxide,
   barium hydroxide,
   lanthanum triisopropoxide,
   scandium triisopropoxide,
   ytterbium triisopropoxide,
   chromium triisopropoxide,
   titanium tetraisopropoxide,
   zirconium tetraisopropoxide,
   iron (III) ethoxide,
   copper (II) ethoxide,
   zinc bis(2-methoxyethoxide).
Water-Soluble Salts of Polyvalent Metals:
   aluminum salicylate,
   aluminum chloride.
Water-Soluble Hydroxides of Polyvalent Metals:
   aluminum hydroxide,
   calcium hydroxide,
   lanthanum hydroxide,
   magnesium hydroxide,
   barium hydroxide.
Water-Soluble Oxides of Polyvalent Metals:
   aluminum oxide.
Complexes of Polyvalent Metals:
   vanadium (III) tetrakisacetylacetonato,
   manganese (III) tetrakisacetylacetonato,
   cobalt (III) tetrakisacetylacetonato,
   nickel (II) tetrakisacetylacetonato, As the source of polyvalent metal ions, further, it is also allowable in the present invention to use a polyvalent metal ion-eluting filler (hereinafter simply called polyvalent metal filler) in addition to the above-mentioned polyvalent metal compounds. That is, the polyvalent metal filler has a function for improving mechanical strength of the cured film, and is advantageous, particularly, from the standpoint of improving abrasion resistance and durability of the cured film.

The polyvalent metal filler may, further, contain monovalent metal ions such as of sodium so far as it is capable of eluting the polyvalent metal ions in the range as described above. If contained in too large amounts, however, the monovalent metal ions affect the ionic crosslinking of the polyvalent metal ions. It is, therefore, desired that the monovalent metal ions are contained in amounts as small as possible. Usually, therefore, it is desired that the content of the monovalent metal ions in the polyvalent metal filler is not larger than 10% by mol and, particularly, not larger than 5% by mol of the content of the polyvalent metal ions.

Elution of the polyvalent metal ions from the polyvalent metal filler is, usually, completed in about 3 hours to 12 hours at room temperature (23° C.) after the preparation of the tooth surface coating material. When the polyvalent metal filler is used, therefore, the amount of the polyvalent metal ions is substantially equal to the amount of the polyvalent metal ions of after 24 hours have passed at room temperature (23° C.) from the preparation, and can be calculated from the total amount of polyvalent metal ions contained in the polyvalent metal filler and the content of the monomer component (A) in the tooth surface coating material.

There is no particular limitation on the above-mentioned polyvalent metal filler provided it is capable of eluting the polyvalent metal ions in amounts in the above-mentioned range. When the polyvalent metal ions are contained in the form of a salt of counter anions capable of being eluted out simultaneously with the polyvalent metal ions, however, it is probable that the eluted and dissociated counter anions may adversely affect the strength of adhesion (this also holds true even when a water-soluble salt of a polyvalent metal is used). In the present invention, therefore, it is desired to use a polyvalent metal filler that does not permit the elution of counter anions simultaneously with the polyvalent metal ions. As the polyvalent metal filler that satisfies the above conditions, there can be exemplified glasses having a skeleton of a chain-like, lamellar or mesh-like structure containing polyvalent metal ions in the gaps of the skeleton.

As the above glasses, there can be preferably used the ones containing oxide glass components, such as aluminosilicate glass, borosilicate glass or soda-lime glass, and the ones containing fluoride glass components, such as zirconium fluoride glass. That is, after having eluted out the polyvalent metal ions, the polyvalent metal filler comprising glasses containing these components turns into porous particles having a mesh-like structure that work to improve the mechanical strength and the strength of adhesion of the cured film formed by using the coating material.

Among the above polyvalent metal fillers according to the present invention, it is desired to use the aluminosilicate glass from the standpoint of strength of the cured film and, most desirably, to use a fluoroaluminosilicate glass which gradually releases fluorine from such a standpoint that the cured film gradually releases fluoride ions that work to reinforce the tooth.

Polyvalent metal ion-eluting property of the polyvalent metal filler can be controlled relying upon the ratio of blending various elements in the filler. For example, if the contents of polyvalent metal ions such as of aluminum, calcium, etc. are increased, the amounts of their elution, generally, increase. Upon varying the content of sodium or phosphorus, further, the amount of elution of the polyvalent metal ions can also be varied. Thus, the polyvalent metal ion-eluting property can be controlled relatively easily.

Elution properties of the polyvalent metal filler can, further, be controlled relying on a generally known method. A representative method comprises treating the polyvalent metal filler with an acid to remove polyvalent metal ions in advance from the filler surface to thereby control the elution properties. This method uses a widely known acid, i.e., inorganic acid such as hydrochloric acid, nitric acid, etc. or organic acid such as maleic acid, citric acid, etc. The concentration of acid and the treating time may be suitably determined depending upon the amount of ions to be removed.

Further the fluoroaluminosilicate glass that is preferred as the polyvalent metal filler may, for example, be the one that is widely used for a dental glass ionomer cement. A generally known fluoroaluminosilicate glass has the following composition as expressed by ionic mass percentage:

silicon; 10 to 33%, particularly, 15 to 25%,
aluminum; 4 to 30%, particularly, 7 to 20%,
alkaline earth metals; 5 to 36%, particularly, 8 to 28%,
alkali metal; 0 to 10%, particularly, 0 to 10%,
phosphorus; 0.2 to 16%, particularly, 0.5 to 8%,
fluorine; 2 to 40%, particularly, 4 to 40%,
oxygen; balance.

It is, further, desired to substitute part or whole of calcium in the above alkaline earth metal by magnesium, strontium or barium. Further, the above alkali metal is, most generally, sodium and which may, desirably, be partly or wholly substituted by lithium or potassium. As required, further, it is allowable to use, as the polyvalent metal filler, a glass in which the aluminum is partly substituted by titanium, yttrium, zirconium, hafnium, tantalum or lanthanum.

There is no particular limitation on the shape of particles of the above polyvalent metal filler; i.e., the particles may be pulverized particles obtained by the ordinary pulverization, spherical particles, or may, as required, be mixed with plate-like or fibrous particles.

It is, further, desired that the polyvalent metal filler has an average particle diameter ($D_{50}$) calculated as volume and measured by, for example, the laser diffraction scattering method in a range of 0.01 µm to 5 µm, particularly, 0.05 µm to 3 µm and, most desirably, 0.1 µm to 2 µm. It is, further, desired that when 0.1 g of the filler is dipped and held in 10 ml of an aqueous solution containing 10% by weight of maleic acid at a temperature of 23° C. for 24 hours, the polyvalent metal ions are eluted in an amount of 5.0 to 500 meq/g of filler and, particularly, 10 to 100 meq/g of filler from the standpoint of easily adjusting the amount of elution of polyvalent metal ions to lie in the above-mentioned range. In this case, too, the amount of polyvalent metal ions can be measured relying on the ICP emission spectroscopy or the atomic absorption spectroscopy. The amount of elution of polyvalent metal ions after 24 hours have passed under the above conditions is hereinafter also called "amount of ion elution in 24 hours".

When the above polyvalent metal filler is used as a source of polyvalent metal ions, an advantage is obtained in that the abrasion resistance and durability of the cured film are further improved as described already accompanied, however, by such a defect that the storage stability may decrease. After the polyvalent metal ions are made present in a predetermined amount in the tooth surface coating material by using the polyvalent metal filler, therefore, the filler from which the polyvalent metal ion have been eluted out may be removed by filtration.

<Volatile Water-Soluble Organic Solvent (C)>

The present invention uses the volatile water-soluble organic solvent (C) to prevent gelation that stems from the polyvalent metal ions (B) that are present in the above-mentioned amount and to improve the storage stability. That is, upon diluting the eluted polyvalent metal ions to a particular concentration with the water-soluble organic solvent (C), it is made possible to store the tooth surface coating material in a one-package state (i.e., in the form of one package) being blended with all components.

The water-soluble organic solvent (C) must be blended in an amount in a range of 30 to 150 parts by mass per 100 parts by mass of the polymerizable monomer component (A) and satisfying a condition represented by the following formula (I), $$\alpha \geq 20 \cdot X \quad (I)$$

wherein α is a blended amount of the water-soluble organic solvent (C) per 100 parts by mass of the polymerizable monomer component (A), and X is the amount of the polyvalent metal ions and is a number representing the amount (meq) thereof per gram of the polymerizable monomer component (A).

If the blended amount of the water-soluble organic solvent (C) is smaller than 30 parts by mass, the tooth surface coating material permeates little into the tooth, and a sufficiently high strength of adhesion cannot be obtained. If the blended amount thereof exceeds 150 parts by mass, on the other hand, the organic solvent tends to remain on the tooth surface unless the air is blown thereto to an excess degree making it difficult to obtain a sufficiently high strength of adhesion. Besides, since the concentration of the adhesive component becomes small, the effective component (curable component) remains in decreased amounts on the tooth surface after having blown the air and, therefore, the strength of adhesion and water-resisting property decrease.

Further, if the condition of the formula (I) is not satisfied (i.e., if α<20·X), the polyvalent metal ions are diluted little and, therefore, the gelation takes place despite the water-soluble organic solvent (C) is contained in an amount in the range of 30 to 150 parts by mass. As a result, it becomes difficult to store the tooth surface coating material in the form of one package blended with all components.

In the present invention, it is desired that the water-soluble organic solvent (C) is blended in an amount in a range of 60 to 100 parts by mass per 100 parts by mass from the standpoint of obtaining a particularly high strength of adhesion to the tooth. It is, further, desired that the blended amount satisfies the following formula (II), $$\alpha \geq 25 \cdot X \quad (II)$$

wherein α and X are as defined in the formula (I).

The tooth surface coating material of the invention is applied onto the tooth surface. Thereafter, the air is blown thereto to volatilize the water-soluble organic solvent (C) prior to being cured by the irradiation with light. That is, upon volatilizing the water-soluble organic solvent (C), the effective component is concentrated on the tooth surface accelerating the ionic crosslinking between the acidic group-containing polymerizable monomer (A1) and the polyvalent metal ions, making it possible to obtain an excellent strength of adhesion to the tooth surface, to improve water-resisting property and to maintain excellent luster on the surface of the cured film. Besides, the tooth surface coating material is effectively cured even in deeply permeated portions of the dentinal tubules. Therefore, the water-soluble organic solvent (C) used in the invention must be soluble in water and, at the same time, must be volatile at room temperature.

In this specification, the word "volatile" stands for that the boiling point under 760 mmHg is not higher than 100° C. and the vapor pressure at 20° C. is not less than 1.0 KPa. Further, the word "water-soluble" stands for that the solubility in water at 20° C. is not less than 20 g/100 ml.

As the volatile water-soluble organic solvent, there can be exemplified methanol, ethanol, n-propanol, isopropyl alcohol, acetone and methyl ethyl ketone. As required, these organic solvents may be used being mixed together. By taking toxicity to the living bodies into consideration, however, it is desired to use ethanol, isopropyl alcohol or acetone.

<Water (D)>

In the present invention, water which is the component (D) works as a solvent for homogeneously dispersing various components therein and, at the same time, is necessary for accelerating the deliming of tooth and the ionic crosslinking of the acidic group-containing polymerizable monomer (A1) with the polyvalent metal ions (B). The water is desirably distilled water or deionized water substantially free of impurities detrimental to storage stability and to medicinal components.

The amount of addition of water which is the component (D) is 3 to 30 parts by mass and, particularly, 5 to 25 parts by mass per 100 parts by mass of the monomer component (A). If the amount of addition of water is smaller than this range, deliming of the tooth and ionic crosslinking become insufficient, and a high strength of adhesion cannot be obtained. If used in amounts larger than the above range, on the other hand, removal of water by the blow of the air decreases after the tooth surface coating material is applied onto the tooth surface; i.e., water remains much on the tooth surface, a sufficiently high strength of adhesion cannot be obtained, and the water-resisting property decreases, too.

<Photopolymerization Initiator (E)>

As the photopolymerization initiator (E) to be added to the tooth surface coating material of the invention, there can be used a compound which can be decomposed by the irradiation with light to form radical species thereof, and a mixture of such a compound and a polymerization accelerator.

Though not limited thereto only, described below are examples of the compound which decomposes upon the irradiation with light to form polymerizable radical species.

α-Diketones:
  camphorquinone,
  benzil,
  α-naphthyl,
  acetonaphthene,
  naphthoquinone,
  1,4-phenanthrenequinone,
  3,4-phenanthrenequinone,
  9,10-phenanthrenequinone.
Thioxanthones:
  2,4-diethylthioxanthone.
α-Aminoacetophenones:
  2-benzyl-dimethylamino-1-(4-morpholinophenyl)-butanone-1,
  2-benzyl-diethylamino-1-(4-morpholinophenyl)-butanone-1,
  2-benzyl-dimethylamino-1-(4-morpholinophenyl)-propanone-1,
  2-benzyl-diethylamino-1-(4-morpholinophenyl)-propanone-1,
  2-benzyl-dimethylamino-1-(4-morpholinophenyl)-pentanone-1, 2-benzyl-diethylamino-1-(4-morpholinophenyl)-pentanone-1.

Acylphosphinoxide Derivatives:
2,4,6-trimethylbenzoyldiphenylphosphinoxide,
bis(2,6-dimethoxybenzoyl)-2,4,4-trimethylpentyl phosphinoxide.

As the polymerization accelerator, further, there can be used tertiary amines, barbituric acids and mercapto compounds. Concrete examples are as described below.

Tertiary Amines:
N,N-dimethylaniline,
N,N-diethylaniline,
N,N-di-n-butylaniline,
N,N-dibenzylaniline,
N,N-dimethyl-p-toluidine,
N,N-diethyl-p-toluidine,
N,N-dimethyl-m-toluidine,
p-bromo-N,N-dimethylaniline,
m-chloro-N,N-dimethylaniline,
p-dimethylaminobenzaldehyde,
p-dimethylaminoacetophenone,
p-dimethylaminobenzoic acid,
p-dimethylaminobenzoic acid ethylester,
p-dimethylaminobenzoic acid amylester,
N,N-dimethylanthranic acid methylester,
N,N-dihydroxyethylaniline,
N,N-dihydroxyethyl-p-toludine,
p-dimethylaminophenetyl alcohol,
p-dimethylaminostilbene,
N,N-dimethyl-3,5-xylidene,
4-dimethylaminopyridine,
N,N-dimethyl-α-naphthylamine,
N,N-dimethyl-β-naphthylamine,
tributylamine,
tripropylamine,
triethylamine,
N-methyldiethanolamine,
N-ethyldiethanolamine,
N,N-dimethylhexylamine,
N,N-dimethyldodecylamine,
N,N-dimethylstearylamine,
N,N-dimethylaminoethyl acrylate,
N,N-dimethylaminoethyl methacrylate,
2,2'-(n-butylimino)diethanol.

Barbituric Acids:
5-butylbarbituric acid,
1-benzyl-5-phenylbarbituric acid.

Mercapto Compounds:
dodecylmercaptane,
pentaerythritoltetrakis(thioglycolate).

There is no particular limitation on the amount of blending the photopolymerization initiator (E) provided it is used in an amount effective for curing the tooth surface coating material, and the amount may be suitably set. Generally, however, the photopolymerization initiator (E) is used in an amount in a range of 0.01 to 10 parts by mass and, particularly, 0.1 to 5 parts by mass per 100 parts by mass of the monomer component (A). If the amount is smaller than 0.01 parts by mass, the polymerization becomes insufficient. If the amount exceeds 10 parts by mass, the strength of the formed polymer decreases, which is not desirable.

<Coloring Agent (F)>

The tooth surface coating material of the invention can be blended with a coloring agent (F) in order to improve aesthetic appearance of the coating after cured. Upon being blended with the coloring agent, the color tone of the obtained cured film can be adjusted. As the coloring agent, there can be used a dye or a pigment that is known per se.

Suitable examples of the dye (or pigment) include Phthalocyanine Blue, Methylene Blue, anthraquinone derivatives, Phloxine BK, Acid Red, Fast Acid Magenta, Phloxine B, Fast Green FCF, Rhodamine B, basic Fuchsine, acidic Fuchsine, Eosine, Etislosine, Safranine, Rose Bengale, hematoxylin, gentiana violet, copper chlorophyll soda, laccaic acid, fluorescein sodium, cochineal, shisonin, talc and titanium white.

These coloring agents can be used in one kind or in two or more kinds in combination. The coloring agent may be added in a suitable amount without any particular limitation by taking the color tone and aesthetic appearance of the tooth surface coating material into consideration. Generally, however, the coloring agent is used in an amount in a range of 0.01 to 1 part by mass and, particularly, 0.02 to 0.5 parts by mass per 100 parts by mass of the monomer component (A) from the standpoint of imparting a color tone to a sufficient degree without adversely affecting other properties.

<Other Blending Agents>

The tooth surface coating material of the present invention can be, further, blended with various known blending agents in addition to the above-mentioned components in ranges in which they do not impair the object of the invention.

In order to further improve the durability of the cured film and its adhesion to the tooth surface (enamel and dentin), for example, an inorganic filler can be added in addition to the above-mentioned polyvalent metal filler. The inorganic filler can be distinguished from the above-mentioned polyvalent metal filler since it does not elute out polyvalent metal ions. Representative examples thereof are composite inorganic oxides such as silica, silica/zirconia, silica/titania and silica/alumina.

Though there is no particular limitation on the particle size, it is desired that the inorganic filler has a primary particle size of not larger than 5 μm, more preferably, 0.001 to 1 μm and, most preferably, 0.01 to 0.5 μm as measured by using an electron microscope. Further, the particles are not at all limited for their shapes, and may be amorphous or may have a spherical shape.

Upon being imparted with hydrophobic property by using a surface-treating agent as represented by a silane coupling agent, the inorganic filler exhibits improved affinity to the polymerizable monomer component (A) and works to further improve the mechanical strength and water-resisting property.

Though not limited thereto only, described below are examples of the silane coupling agent that can be used for imparting hydrophobic property.

Silane Coupling Agents:
methyltrimethoxysilane,
methyltriethoxysilane,
methyltrichlorosilane,
dimethyldichlorosilane,
trimethylchlorosilane,
vinyltrimethoxysilane,
vinyltriethoxysilane,
vinyltrichlorosilane,
vinyltriacetoxysilane,
vinyltris(β-methoxyethoxy)silane,
γ-methacryloyloxypropyltrimethoxysilane,
γ-methacryloyloxypropyltris(β-methoxyethoxy)silane,
γ-chloropropyltrimethoxysilane,
γ-chloropropylmethyldimethoxysilane,
γ-glycidoxypropyltrimethoxysilane,
γ-glycidoxypropylmethyldiethoxysilane,
β-(3,4-epoxycyclohexyl)ethyltrimethoxysilane, N-phenyl-γ-aminopropyltrimethoxysilane, and hexamethyldisilazane.

The inorganic filler works to improve the durability and strength of adhesion of the cured film but also tends to decrease the storage stability. It is, therefore, desired that the inorganic filler is added in small amounts, for example, in a range of 2 to 20 parts by mass and, particularly, 5 to 10 parts by mass per 100 parts by mass of the monomer component (A). If the amount is smaller than the above range, advantages by the addition of the inorganic filler are not obtained to a sufficient degree. If used in amounts larger than the above range, on the other hand, the viscosity so increases as to impair the permeation into the tooth and to decrease the storage stability.

As the blending agents other than the above inorganic filler, there can be exemplified organic viscosity-imparting agents such as polyvinyl pyrrolidone, carboxymethyl cellulose and polyvinyl alcohol. As required, further, it is allowable to selectively use various additives such as ultraviolet absorber, dye, antistatic agent, fluorescent agent and perfume. It needs not be pointed out that these blending agents, too, are added in such amounts that do not impair the storage stability or properties of the cured film.

The above components are mixed together as one liquid so as to be used as the tooth surface coating material of the invention. The mixing method may comply with a variety of methods that have been placed in practice for the known curable compositions. Usually, the components to be blended are all weighed and may be mixed well together until they turn into a homogeneous solution under the illumination of inactive light such as red light.

EXAMPLES

The invention will now be concretely described by way of Examples and Comparative Examples to which only, however, the invention is in no way limited. The kinds of components used in the following Examples and the methods of testing and evaluating the properties were as described below.

[Acidic Group-Containing Polymerizable Monomers (A1)]
  PM: A mixture of 2-methacryloyloxyethyldihydrogen phosphate and bis(2-methacryloyloxyethyl)hydrogen phosphate
  MDP: 10-Methacryloyloxydecyldihydrogen phosphate

[Polymerizable Monomers (A2) without Acidic Group]
D26E: 2,2-Bis(4-(methacryloxyethoxy)phenyl)propane
BisGMA: 2,2'-Bis[4-(2-hydroxy-3-methacryloxypropoxy)phenyl]propane
3G: Triethylene glycol dimethacrylate
HEMA: 2-Hydroxyethyl methacrylate

[Polyvalent Metal Ion (B) Sources]
  Polyvalent Metal Ion-Eluting Fillers.
  F-1: Polyvalent metal ion-eluting filler obtained in Preparation Example 1,
    Average particle diameter: 0.5 μm,
    Amount of ions eluted out in 24 hours: 10 meq/g of filler
  F-2: Polyvalent metal ion-eluting filler obtained in Preparation Example 2,
    Average particle diameter: 0.5 μm,
    Amount of ions eluted out in 24 hours: 25 meq/g of filler
  F-3: Polyvalent metal ion-eluting filler obtained in Preparation Example 3,
    Average particle diameter: 0.5 μm,
    Amount of ions eluted out in 24 hours: 50 meq/g of filler
  Polyvalent Metal Compounds.
  Al(O-iPr)3: Aluminum triisopropoxide
  La(O-iPr)3: Lanthanum triisopropoxide
  Ti(O-iPr)4: Titanium tetraisopropoxide
  La(OH)3: Lanthanum hydroxide

[Volatile Water-Soluble Organic Solvents (C)]
  Et-OH: Ethyl alcohol
  IPA: Isopropyl alcohol

[Photopolymerization Initiators (E)]
CQ: Camphorquinone
DMBE: Ethyl N,N-dimethyl-p-aminobenzoate
TPO: 2,4,6-Trimethylbenzoyldiphenylphosphinoxide

[Coloring Agents (Dyes, Pigments)]
  FCB: Phthalocyanine blue
  TW: Titanium white

[Other Components (Inorganic Fillers)]
  Si—Ti: Spherical silica/titania treated with γ-methacryloyloxypropyltrimethoxysilane so as to be imparted with hydrophobic property
  Si-1: Amorphous silica (particle diameter, 0.02 μm) treated with methyltrichlorosilane
  Si-2: A mixture of spherical silica/zirconia (particle diameter, 0.4 μm) and spherical silica/titania (particle diameter, 0.08 μm) at a mass ratio of 70:30 (spherical silica/zirconia and spherical silica/titania are both treated with γ-methacryloyloxypropyltrimethoxysilane so as to be imparted with hydrophobic property)

[Method of Measuring the Strength of Adhesion]
Preparation of a Test Piece:

Within 24 hours after the slaughter, a bovine foretooth was pulled out, and the enamel surface and the dentin surface were ground paralleling to the labial face by using a #600 emery paper while pouring water. Next, the compressed air was blown onto the surface that was ground and exposed for about 10 seconds to dry the surface to thereby prepare a model tooth.

A double-sided adhesive tape having a hole of 3 mm in diameter perforated therein was fixed to the surface of the model and, thereafter, a paraffin wax (thickness of 0.5 mm) having a hole of 8 mm in diameter perforated therein was fixed thereto in concentric with the hole of the double-sided tape to form a mimic cavity.

A sample tooth surface coating material was applied into the mimic cavity, left to stand for 20 seconds and, thereafter, the compressed air was blown thereto for about 10 seconds to dry.

Next, the tooth surface coating material was cured by the irradiation with light from a visible ray irradiator (Power Light, manufactured by Tokuyama Dental Co.) for 10 seconds.

Further, a dental composite resin (Palfique Estelite Σ, manufactured by Tokuyama Dental Co.) was applied thereon, and was irradiated with light by using the above visible ray irradiator for 30 seconds to prepare an adhesion test piece.

Measurement of Strength of Adhesion:

After dipped in water of 37° C. for 24 hours, the above adhesion test piece was pulled by using a tension tester (Autograph manufactured by Shimazu Seisakusho Co.) at a crosshead speed of 2 mm/min to measure the tensile adhesive strength between the dentin and the composite resin. Four test pieces were measured for their tensile adhesive strengths per a test relying upon the above method, and an average value thereof was regarded as an initial adhesive strength.

[Evaluation of Storage Stability]

A sample tooth surface coating material was prepared and was stored in an incubator maintained at 37° C. for one month. By using the thus stored tooth surface coating material, the strength of adhesion was measured by the same method as the above method of measuring the strength of adhesion, and was compared with the strength of adhesion of before being stored at 37° C.

[Methods of Measuring the Flexural Strength and Water-Resisting Property of the Cured Body]

Preparation of the Cured Body:

A frame made of a polytetrafluoroethylene was filled with a tooth surface coating material from which the volatile organic solvent has been volatilized by the blow of the compressed air, and a polypropylene film was press-adhered onto one surface of the tooth surface coating material. The tooth surface coating material was irradiated with light for 30 seconds by using the Tokuso Power Light that was contacted to the polypropylene while varying the place of irradiation so that the whole of the tooth surface coating material was irradiated with light. This operation was conducted three times. Next, the polypropylene was similarly press-adhered onto the opposite surface of the tooth surface coating material, and light was similarly irradiated for 30 seconds and three times to obtain a cured body that served as a test piece.

Evaluating the Flexural Strength:

The cured body was dipped in water of 37° C. for 24 hours, and was shaped into a square pole of 2×2×25 mm by using a #800 water-resistant polishing paper. The thus obtained test piece was fitted onto a tester (Autograph AG5000D manufactured by Shimazu Seisakusho Co.) and was measured for its three-point flexural strength maintaining a distance between the fulcrums of 20 mm and at a crosshead speed of 1 mm/min. Five test pieces were measured for their three-point flexural strengths per a test, and their average value was regarded as the initial flexural strength.

Evaluating the Water-Resisting Property:

The test pieces for measuring the three-point flexural strengths prepared by the above method were left to stand in water of 37° C. for one month and were, thereafter, measured for their three-point flexural strengths to evaluate the water-resisting properties in comparison with the initial flexural strengths.

[Evaluating the Maintenance of Luster on the Surface of the Cured Film]

Preparation of a Test Piece:

A model tooth was prepared in the same manner as the one used for the measurement of the strength of adhesion.

Next, the sample tooth surface coating material was applied to the whole surface of the model that was ground, left to stand for 20 seconds and was dried by blowing the compressed air for about 10 seconds.

Next, the tooth surface coating material was cured by irradiating light by using the visible ray irradiator (Power Light manufactured by Tokuyama Dental Co.) for 10 seconds. The surface of the formed cured film was quickly wiped to remove the unpolymerized layer formed on the surface of the cured film, and a test piece was obtained.

Evaluation of the Maintenance of Luster:

Luster on the surface of the cured film was evaluated on the following basis:

○: Luster could be confirmed on the surface of the cured film.

X: No luster on the surface of the cured film, i.e., cloudy surface. In the worst case, the tooth surface coating material had not been sufficiently cured, and the surface was pulpy.

Further, after left to stand in water of 37° C. for one month, the test pieces were evaluated for their luster on the surfaces of the cured films and were compared with the luster of before being left to stand in water.

[Measuring the Rate of Polymerization on the Surface of the Cured Body]

The tooth surface coating material after the volatile organic solvent has been volatilized by blowing the compressed air was flown into a mold of a polytetrafluoroethylene (0.5 mm thick) having a cylindrical hole of a diameter of 6 mm perforated therein, and an infrared absorption (IR) spectrum on the surface of the tooth surface coating material was measured relying on the one-time reflection (ATR) method by using an infrared spectroscopic analyzer ("Spectrum One" manufactured by Perkin Elmer Co.).

Next, the whole of the tooth surface coating material was irradiated with light by using the visible light irradiator for 30 seconds to thereby obtain a cured body.

The IR spectrum on the surface of the cured body was measured by the same method as the above-mentioned method, and the rate of polymerization on the surface of the cured body was calculated from the IR spectra of before the curing and after the curing (cured body) in compliance with the following formula, $$\text{Rate of polymerization \%} = 100 - (Pcc \cdot Qco/Pco) \cdot 100$$

wherein $Pcc$ is a C=C peak intensity of the cured body, $Pco$ is a C=O peak intensity of the cured body, and $Qco$ is a C=O peak intensity of the coating material before being cured.

[Measuring the Amount of Polyvalent Metal Ions]

The components were mixed together to prepare a sample tooth surface coating material which was then stirred for 24 hours. Thereafter, 0.2 g of the coating material was weighed and put into a 100-ml sample tube and was diluted into 1% with an isopropanol (IPA).

By using an ICP (inductively coupled plasma) emission spectroscopy, the diluted solution was measured for its Al, La and Ca ion concentrations (mmols/g) contained per gram of the polymerizable monomer component (A). The obtained ion concentrations were multiplied by their respective ionic valencies, and the sum thereof was regarded to be the amount of ionic bonds, i.e., the amount of polyvalent ions/meq per gram of the component (A).

The polyvalent metal ions eluted out from the fillers used in Examples and in Comparative Examples were all Al, La and Ca ions, but no other ions were detected.

[Testing the Abrasion Using a Toothbrush]

Preparation of a Test Piece:

A model tooth having a dentin exposed on the surface was prepared in the same manner as the one used for the measurement of the strength of adhesion.

The sample tooth surface coating material was applied onto the whole surface of the dentin of the model and was irradiated with light by using the visible light irradiator for 10 seconds to form a cured film of the tooth surface coating material.

A dental composite resin (Estelite LV High Flow manufactured by Tokuyama Dental Co.) was applied onto half the surface of the model on which the cured film has been formed, and was irradiated with light by using the visible light irradiator for 30 seconds to form a composite resin layer having a thickness of about 100 μm to thereby obtain a test piece. FIG. 1 is a schematic sectional view of the test piece.

Abrasion Test:

A tooth-brushing agent (White & White manufactured by Lion Co.) containing water as a solvent was put to a toothbrush (Robinson brush) fitted to a dental turbine, and the surface of the test piece was abraded 10,000 times by using the toothbrush under a load of 400 g as shown in FIG. 1.

The composite resin was applied onto the whole surface of the test piece after it has been abraded, and was cured.

Next, by using a diamond cutter, the test piece was cut perpendicularly to the abraded surface. The cut surface was mirror polished and was observed by using a laser microscope.

From the observation using the microscope, a step was measured from the upper surface of the cured film of the sample tooth surface coating material which was covered by the composite resin layer formed on the half surface of the model down to the abraded surface of the cured film of the tooth surface coating material to evaluate the abrasion resistance (durability) relying on the size of the step. That is, the smaller the step, the higher the abrasion resistance of the cured film exhibiting excellent durability.

[Evaluating the Dentinal Tubule Occlusion]

Preparation of a Model of Hypersensitivity:

A fresh bovine tooth was polished by using a #600 water-resistant polishing paper so that the dentin was exposed. Next, the exposed surface of the dentin was cleaned and polished for 3 minutes by using the Robinson brush fitted to the dental turbine and the tooth-brushing agent. The thus treated bovine tooth was washed by using an ultrasonic washing device for one hour to prepare a model of hypersensitivity.

Figure 2:
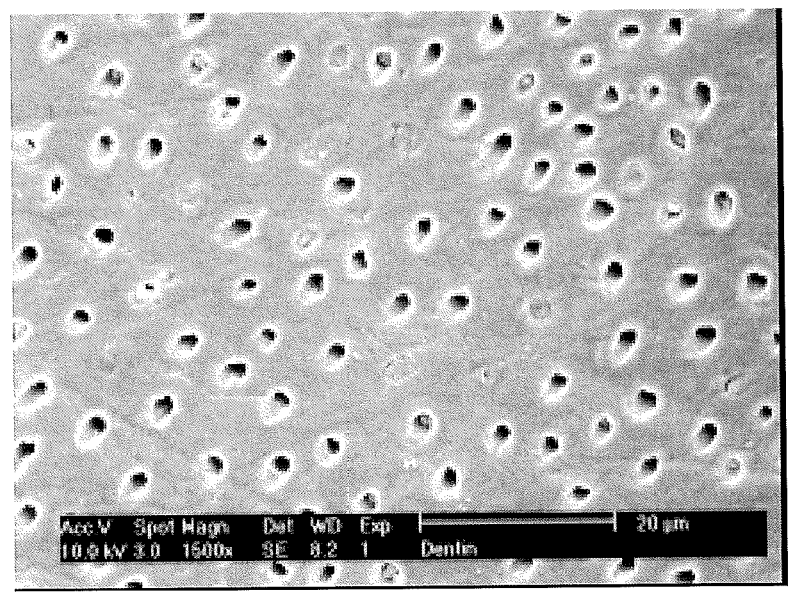
FIG. 2 is an SEM photograph showing the surface of a model of hypersensitive dentin used for testing the dentinal tubule occlusion.

FIG. 2 is a microscope photograph of the surface of the model of hypersensitive dentin.

As shown in the microscope photograph of FIG. 2, a number of dentinal tubules were exposed on the surface of the dentin and their percentage of opening was about 80%.

Evaluating the Occlusion:

The sample tooth surface coating material was applied onto the surface of the model of hypersensitive dentin prepared above and was irradiated with light by using the visible light irradiator for 10 seconds to form a cured film of the tooth surface coating material.

The composite resin was applied onto the whole treated surface of the model on which the cured film has been formed, and was cured. Thereafter, by using a diamond cutter, the model was cut perpendicularly to the surface of the dentin, and the cut surface was mirror polished.

Next, the model was dipped in a 6 N hydrochloric acid solution for 30 seconds and was, further, dipped in an aqueous solution containing 1% of sodium hypochlorite for 10 minutes so that the surface side of the dentin was dissolved. After dried, the cut surface was observed by using the SEM to evaluate the occlusion of dentinal tubules. When the tooth surface coating material has deeply permeated into the dentinal tubules and was favorably cured in the deeply permeated portions, tags of the resin had been formed much on the surface on where the dentin has dissolved, and the occlusion of dentinal tubules could be evaluated based on the presence of the tags.

Figure 3:
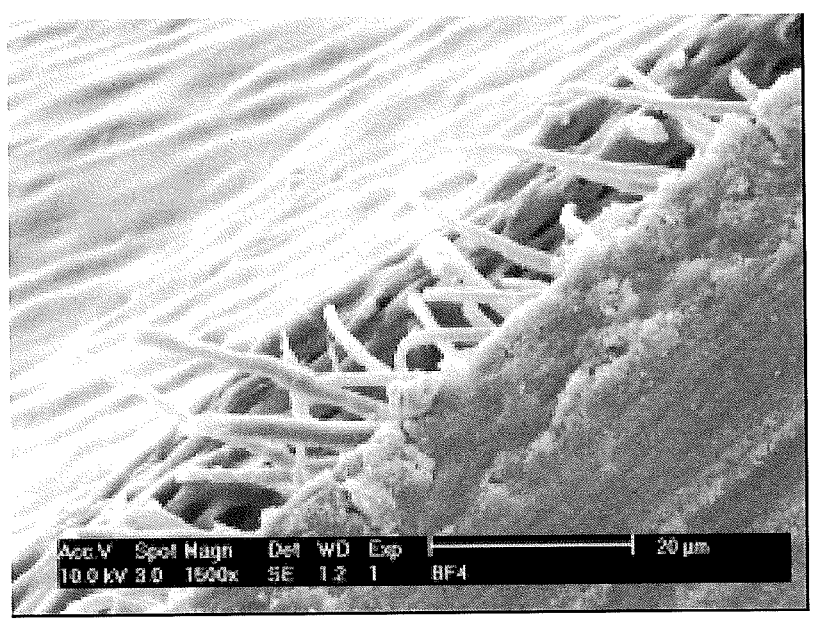
FIG. 3 is an SEM photograph of a cross section of when a test piece obtained by forming a cured film of the tooth surface coating material (Example 1) of the invention on the surface of a model of hypersensitive dentin is treated with an acid on the cross section thereof to dissolve and remove the surface portion of the dentin.

FIG. 3 is an SEM photograph in Example 3. When the tags were formed, ten tags randomly selected were measured for their lengths (lengths from the surface of the dentin to the ends of the tags) and their average values were compared.

Preparation of the Polyvalent Metal Fillers

Preparation Example 1

A fluoroaluminosilicate glass powder (Tokuso Ionomer manufactured by Tokuyama Dental Co.) was pulverized into an average particle diameter of 0.5 µm by using a wet continuous-type ball mill (New My-Mill manufactured by Mitsui Kozan Co.). Thereafter, the filler surfaces were treated with 5.0 N hydrochloric acid in an amount of 20 g per gram of the powder for 40 minutes to obtain a polyvalent metal filler (F-1).

0.1 Gram of the thus obtained filler was dipped in 10 ml of an aqueous solution containing 10% by weight of maleic acid and maintained at a temperature of 23° C. After 24 hours have passed, the amount of polyvalent metal ions that have eluted out was analyzed to be 10 meq/g of filler (amount of ion elution in 24 hours).

Preparation Example 2

The fluoroaluminosilicate glass powder (Tokuso Ionomer manufactured by Tokuyama Dental Co.) was pulverized into an average particle diameter of 0.5 µm by using the wet continuous-type ball mill (New My-Mill manufactured by Mitsui Kozan Co.). Thereafter, the filler surfaces were treated with 5.0 N hydrochloric acid in an amount of 20 g per gram of the powder for 20 minutes to obtain a polyvalent metal filler (F-2).

The amount of ion elution of the polyvalent metal filler in 24 hours was 25 meq/g of filler.

Preparation Example 3

The fluoroaluminosilicate glass powder (Tokuso Ionomer manufactured by Tokuyama Dental Co.) was pulverized into an average particle diameter of 0.5 µm by using the wet continuous-type ball mill (New My-Mill manufactured by Mitsui Kozan Co.) to obtain a polyvalent metal filler (F-3). The amount of ion elution of the polyvalent metal filler in 24 hours was 50 meq/g of filler.

Example 1

The components were mixed together according to the following recipe to prepare a tooth surface coating material of the invention.

Component (A1): PM, 1.5 g
Component (A2): D26E, 5.0 g
    HEMA, 3.5 g
Component (B): F-2, 1.0 g
Component (C): acetone, 5.0 g
Component (D): water, 1.5 g
Component (E): CQ, 0.1 g
    DMBE, 0.15 g The tooth surface coating material immediately after the preparation was evaluated for its strength of adhesion to the enamel and dentin, storage stability, flexural strength and water-resisting property of the cured body, maintenance of luster on the surface of the cured film and rate of polymerization of the surface of the cured film. The components of the tooth surface coating material were as shown in Table 1, and the evaluated results were as shown in Table 3.

Examples 2 to 26

The tooth surface coating materials were prepared in the same manner as in Example 1 but changing the recipe of components as shown in Table 1 or 2, and were evaluated. The evaluated results were as shown in Tables 3 and 4.

Comparative Examples 1 to 14

The tooth surface coating materials were prepared in the same manner as in Example 1 but changing the recipe of components as shown in Table 5, and were evaluated. The evaluated results were as shown in Table 6.

TABLE 1

Tooth surface coating material composition/pts. by mass

| | (A)*1 | | | | | (B)*1 | | | | (C)*1 | | | (D)*1 | (E)*1 | | | Pigments | | Filler*4 | |
|---|---|---|---|---|---|---|---|---|---|---|---|---|---|---|---|---|---|---|---|---|
| | (A1) | | | (A2) | | | | | | | | | | | | | | | | |
| Ex. No. | PM | MDP | D26E | BisGMA | 3G | HEMA | F-1 | F-2 | F-3 | *2 | EtOH | IPA | *3 | CQ | TPO | DMBE | FCB | TW | Si-1 | Si-2 |
| 1 | 15 | | | | | 50 | 35 | | | 10 | 50 | | | 15 | 1 | 1.5 | | | | |
| 2 | 15 | | | | | 50 | 35 | | | 10 | 65 | | | 15 | 1 | 1.5 | 0.01 | 0.1 | | |
| 3 | 15 | | | | | 50 | 35 | | | 10 | 85 | | | 15 | 1 | 1.5 | 0.01 | 0.1 | | |
| 4 | 15 | | | | | 50 | 35 | | | 10 | 140 | | | 15 | 1 | 1.5 | 0.01 | 0.1 | | |
| 5 | 15 | | | | | 50 | 35 | | | 20 | 100 | | | 15 | 1 | 1.5 | 0.01 | 0.1 | | |
| 6 | | 15 | | | | 50 | 35 | | | 10 | 85 | | | 15 | 1 | 1.5 | 0.01 | 0.1 | | |
| 7 | 15 | | | | | 50 | 35 | 15 | | | 50 | | | 15 | 1 | 1.5 | 0.01 | 0.1 | | |
| 8 | 15 | | | | | 50 | 35 | | 8 | | 90 | | | 15 | 1 | 1.5 | 0.01 | 0.1 | | |
| 9 | 25 | | | | | 50 | 25 | | | 10 | 85 | | | 15 | 1 | 1.5 | 0.01 | 0.1 | | |
| 10 | 25 | | | 30 | 20 | 25 | | | | 10 | 85 | | | 15 | 1 | 1.5 | 0.01 | 0.1 | | |
| 11 | 25 | | | 30 | 20 | 25 | | | | 10 | | 85 | | 15 | 1 | 1.5 | 0.01 | 0.1 | | |
| 12 | 25 | | | 30 | 20 | 25 | | | | 10 | | | 85 | 15 | 1 | 1.5 | 0.01 | 0.1 | | |
| 13 | 25 | | | 30 | 20 | 25 | | | | 10 | | | 85 | 15 | | 1 | 0.01 | 0.1 | | |
| 14 | 25 | | | 30 | 20 | 25 | | | | 10 | | | 85 | 15 | 1 | 1 | 1 | 0.01 | 0.1 | |

*1Component
*2Acetone
*3Water
*4Inorganic fillers

TABLE 2

Tooth surface coating material composition/pts. by mass

| | (A)*1 | | | | | (B)*1 | | | | (C)*1 | | | (D)*1 | (E)*1 | | | Pigments | | Filler*4 | |
|---|---|---|---|---|---|---|---|---|---|---|---|---|---|---|---|---|---|---|---|---|
| | (A1) | | | (A2) | | | | | | | | | | | | | | | | |
| Ex. No. | PM | MDP | D26E | BisGMA | 3G | HEMA | F-1 | F-2 | F-3 | *2 | EtOH | IPA | *3 | CQ | TPO | DMBE | FCB | TW | Si-1 | Si-2 |
| 15 | 25 | | | 30 | 20 | 25 | | | | 10 | 85 | | | 15 | 4 | 4 | 0.01 | 0.1 | | |
| 16 | 45 | | 35 | | | 20 | | | | 10 | 85 | | | 15 | 1 | 1.5 | 0.01 | 0.1 | | |
| 17 | 10 | | 50 | | | 40 | | | | 10 | 85 | | | 15 | 1 | 1.5 | 0.01 | 0.1 | | |
| 18 | 15 | | | | | 50 | 35 | 17 | | | 85 | | | 15 | 1 | 1.5 | 0.01 | 0.1 | | |
| 19 | 15 | | | | | 50 | 35 | | | 3 | 85 | | | 15 | 1 | 1.5 | 0.01 | 0.1 | | |
| 20 | 15 | | | | | 50 | 35 | | | 10 | 85 | | | 5 | 1 | 1.5 | 0.01 | 0.1 | | |
| 21 | 15 | | | | | 50 | 35 | | | 10 | 85 | | | 25 | 1 | 1.5 | 0.01 | 0.1 | | |
| 22 | 15 | | | | | 50 | 35 | 5 | | | 35 | | | 15 | 1 | 1.5 | 0.01 | 0.1 | | |
| 23 | 15 | | | | | 50 | 35 | | 12 | | 140 | | | 15 | 1 | 1.5 | 0.01 | 0.1 | | |
| 24 | 15 | | | | | 50 | 35 | | | 10 | 55 | | | 15 | 1 | 1.5 | 0.01 | 0.1 | 10 | |
| 25 | 25 | | | 30 | 20 | 25 | | | | 10 | 85 | | | 15 | 1 | 1.5 | 0.01 | 0.1 | 10 | |
| 26 | 25 | | | 30 | 20 | 25 | | | | 10 | 85 | | | 15 | 1 | 1.5 | 0.01 | 0.1 | | 20 |

*1Component
*2Acetone
*3Water
*4Inorganic fillers

TABLE 3

| | | | | Strength of adhesion/MPa(S.D.) | | | | Flexural strength of the cured body/MPa (standard deviation) | |
|---|---|---|---|---|---|---|---|---|---|
| | | | Amount of solvent added | Initially | | After stored at 37° C. for a month | | Initially | After stored in water at 37° C. for a month |
| Ex. No. | *1 X meq | *2 20X | | Enamel | Dentin | Enamel | Dentin | | |
| 1 | 2.4 | 48 | 50 | 15.7(3.2) | 14.8(4.1) | 11.8(2.1) | 10.9(2.9) | 105.4(7.2) | 102.0(4.2) |
| 2 | 2.4 | 48 | 65 | 21.7(2.9) | 20.1(3.6) | 19.4(2.1) | 19.0(1.8) | 99.2(3.4) | 96.7(4.5) |
| 3 | 2.4 | 48 | 85 | 22.7(2.9) | 21.1(3.6) | 21.8(2.1) | 20.8(1.8) | 96.5(3.8) | 90.5(3.7) |
| 4 | 2.4 | 48 | 140 | 14.6(2.2) | 15.2(3.3) | 14.2(2.9) | 14.5(2.1) | 79.5(5.2) | 73.7(3.1) |
| 5 | 4.6 | 92 | 100 | 16.8(3.2) | 17.5(2.0) | 12.3(3.0) | 12.0(4.2) | 97.4(2.9) | 96.3(4.0) |
| 6 | 2.2 | 44 | 85 | 18.2(2.2) | 19.0(3.3) | 17.6(3.2) | 18.6(2.3) | 98.4(5.2) | 92.5(3.9) |
| 7 | 1.6 | 32 | 50 | 16.5(2.6) | 17.3(2.1) | 16.8(2.5) | 16.2(2.0) | 82.8(3.0) | 72.6(3.1) |
| 8 | 4.2 | 84 | 90 | 17.0(1.7) | 17.5(3.1) | 13.7(2.2) | 12.8(1.7) | 101.5(6.2) | 99.6(6.1) |

TABLE 3-continued

| | | | | | | | | | |
|---|---|---|---|---|---|---|---|---|---|
| 9 | 2.4 | 48 | 85 | 21.0(2.1) | 20.4(1.3) | 20.6(2.1) | 19.8(3.3) | 109.5(5.5) | 106.9(4.2) |
| 10 | 2.4 | 48 | 85 | 19.8(3.4) | 21.2(4.1) | 19.2(1.4) | 20.7(2.3) | 103.9(1.9) | 100.9(3.0) |
| 11 | 2.2 | 44 | 85 | 19.3(3.2) | 19.2(2.0) | 18.8(3.2) | 18.0(3.3) | 101.4(3.2) | 99.8(3.4) |
| 12 | 2.6 | 52 | 85 | 20.2(2.2) | 19.5(3.0) | 19.9(1.9) | 18.2(2.1) | 107.2(4.0) | 100.4(3.0) |
| 13 | 2.4 | 48 | 85 | 18.9(2.1) | 22.1(3.2) | 18.5(2.8) | 21.6(3.0) | 104.1(3.9) | 100.8(3.2) |
| 14 | 2.6 | 52 | 85 | 22.3(1.7) | 21.0(2.4) | 21.3(2.9) | 20.5(4.2) | 106.3(2.2) | 102.9(4.4) |

| Ex. No. | Luster on the surface of the cured film Initially | Luster on the surface of the cured film After stored in water at 37° C. for a month | Polymerization rate of the cured film surface/% |
|---|---|---|---|
| 1 | ○ | ○ | 82.3(1.2) |
| 2 | ○ | ○ | 80.5(1.3) |
| 3 | ○ | ○ | 79.4(0.8) |
| 4 | ○ | ○ | 72.4(2.0) |
| 5 | ○ | ○ | 84.4(1.5) |
| 6 | ○ | ○ | 81.2(1.4) |
| 7 | ○ | ○ | 74.3(2.2) |
| 8 | ○ | ○ | 80.6(1.7) |
| 9 | ○ | ○ | 83.8(2.2) |
| 10 | ○ | ○ | 81.2(1.6) |
| 11 | ○ | ○ | 80.3(0.8) |
| 12 | ○ | ○ | 84.0(0.9) |
| 13 | ○ | ○ | 82.7(1.1) |
| 14 | ○ | ○ | 81.7(1.2) |

*[1] Amount of ions; Amounts of polyvalent metal ions eluted out into the adhesive and represented as amounts of ions/meq per a gram of the component (A).
*[2] Required amount of solvent; Minimum amounts of the volatile water-soluble organic solvent (parts by mass) necessary for storing the adhesive in the form of one package.

TABLE 4

| Ex. No. | *[1] X meq | *[2] 20X | Amount of solvent added | Strength of adhesion/MPa(S.D.) Initially Enamel | Strength of adhesion/MPa(S.D.) Initially Dentin | Strength of adhesion/MPa(S.D.) After stored at 37° C. for a month Enamel | Strength of adhesion/MPa(S.D.) After stored at 37° C. for a month Dentin | Flexural strength of the cured body/MPa (standard deviation) Initially | Flexural strength of the cured body/MPa (standard deviation) After stored in water at 37° C. for a month |
|---|---|---|---|---|---|---|---|---|---|
| 15 | 2.6 | 52 | 85 | 16.4(3.0) | 15.8(1.3) | 15.8(3.2) | 14.9(2.1) | 90.7(3.2) | 85.6(4.1) |
| 16 | 2.4 | 48 | 85 | 15.6(2.2) | 16.3(3.1) | 14.8(1.7) | 15.4(2.8) | 82.8(4.9) | 72.9(4.1) |
| 17 | 2.6 | 52 | 85 | 14.8(2.1) | 15.6(1.7) | 14.0(1.9) | 14.8(2.2) | 99.8(3.9) | 97.5(2.9) |
| 18 | 1.4 | 28 | 85 | 17.8(2.1) | 18.6(2.1) | 17.5(2.0) | 19.0(2.2) | 77.9(3.9) | 69.9(4.9) |
| 19 | 1.4 | 28 | 85 | 18.3(2.0) | 17.9(1.9) | 18.0(2.2) | 18.5(1.8) | 79.0(5.5) | 68.2(4.7) |
| 20 | 2.2 | 44 | 85 | 14.8(3.2) | 16.8(2.0) | 14.4(1.6) | 15.9(2.2) | 98.9(3.0) | 97.7(3.3) |
| 21 | 2.4 | 48 | 85 | 15.0(3.2) | 15.2(2.6) | 14.5(1.2) | 15.0(1.8) | 82.8(4.0) | 70.5(6.3) |
| 22 | 1.5 | 30 | 35 | 16.3(2.9) | 15.8(4.1) | 11.8(1.8) | 10.2(2.2) | 76.2(4.9) | 68.9(3.9) |
| 23 | 6.1 | 122 | 140 | 15.2(4.0) | 16.2(3.9) | 12.9(3.0) | 11.7(2.0) | 92.9(5.2) | 90.8(3.9) |
| 24 | 2.4 | 48 | 55 | 20.4(2.1) | 18.2(1.1) | 16.1(3.1) | 16.8(2.6) | 102.8(4.0) | 100.5(5.2) |
| 25 | 2.1 | 42 | 85 | 20.8(2.2) | 19.9(2.3) | 19.1(3.0) | 19.1(1.2) | 104.8(6.1) | 102.9(4.1) |
| 26 | 2.3 | 46 | 85 | 20.0(1.5) | 20.5(3.1) | 19.9(1.8) | 19.6(2.7) | 107.6(3.9) | 100.9(5.1) |

| Ex. No. | Luster on the surface of the cured film Initially | Luster on the surface of the cured film After stored in water at 37° C. for a month | Polymerization rate of the cured film surface/% |
|---|---|---|---|
| 15 | ○ | ○ | 75.6(1.0) |
| 16 | ○ | ○ | 74.2(0.6) |
| 17 | ○ | ○ | 80.4(1.6) |
| 18 | ○ | ○ | 71.9(1.0) |
| 19 | ○ | ○ | 72.1(1.3) |
| 20 | ○ | ○ | 81.3(0.2) |
| 21 | ○ | ○ | 73.8(0.8) |
| 22 | ○ | ○ | 71.2(1.2) |
| 23 | ○ | ○ | 81.3(0.9) |
| 24 | ○ | ○ | 82.3(1.0) |

TABLE 4-continued

| | | | |
|---|---|---|---|
| 25 | ○ | ○ | 81.5(2.0) |
| 26 | ○ | ○ | 80.8(0.7) |

[1] Amount of ions; Amounts of polyvalent metal ions eluted out into the adhesive and represented as amounts of ions/meq per a gram of the component (A).
[2] Required amount of solvent; Minimum amounts of the volatile water-soluble organic solvent (parts by mass) necessary for storing the adhesive in the form of one package.

TABLE 5

Tooth surface coating material composition/pts. by mass

| Comp. Ex. No. | (A)[1] | | | | | (B)[1] | | | [3] | (C)[1] | | (D)[1] | (E)[1] | Pigments | [2] |
|---|---|---|---|---|---|---|---|---|---|---|---|---|---|---|---|
| | (A1) | (A2) | | | | | | | | | | | | | |
| | PM | D26E | BisGMA | 3G | HEMA | F-1 | F-2 | F-3 | | EtOH | IPA | [4] | CQ | DMBE | FCB | TW |
| 1 | 15 | 50 | | | 35 | 10 | | | 40 | | | 15 | 1 | 1.5 | | |
| 2 | 15 | 50 | | | 35 | 20 | | | 60 | | | 15 | 1 | 1.5 | | |
| 3 | | 65 | | | 35 | 10 | | | 85 | | | 15 | 1 | 1.5 | 0.01 | 0.1 |
| 4 | 2 | 63 | | | 35 | 10 | | | 85 | | | 15 | 1 | 1.5 | 0.01 | 0.1 |
| 5 | 15 | 50 | | | 35 | | | | 85 | | | 15 | 1 | 1.5 | 0.01 | 0.1 |
| 6 | 15 | 50 | | | 35 | 5 | | | 85 | | | 15 | 1 | 1.5 | 0.01 | 0.1 |
| 7 | 15 | 50 | | | 35 | | | 16 | 135 | | | 15 | 1 | 1.5 | 0.01 | 0.1 |
| 8 | 15 | 50 | | | 35 | 10 | | | 85 | | | | 1 | 1.5 | 0.01 | 0.1 |
| 9 | 15 | 50 | | | 35 | 10 | | | 85 | | | 0.5 | 1 | 1.5 | 0.01 | 0.1 |
| 10 | 15 | 50 | | | 35 | 10 | | | 85 | | | 45 | 1 | 1.5 | 0.01 | 0.1 |
| 11 | 15 | 50 | | | 35 | 10 | | | | | | 15 | 1 | 1.5 | 0.01 | 0.1 |
| 12 | 15 | 50 | | | 35 | 10 | | | 25 | | | 15 | 1 | 1.5 | 0.01 | 0.1 |
| 13 | 15 | 50 | | | 35 | 10 | | | 160 | | | 15 | 1 | 1.5 | 0.01 | 0.1 |
| 14 | 15 | 50 | | | 35 | 10 | | | 85 | | | 15 | | | 0.01 | 0.1 |

[1] Component
[2] Other components
[3] Acetone
[4] Water

TABLE 6

| Comp. Ex. No. | [1] X meq | [2] 20X | Amount of solvent added | Strength of adhesion/MPa (S.D.) | | | | Flexural strength of the cured body/MPa (standard deviation) | |
|---|---|---|---|---|---|---|---|---|---|
| | | | | Initially | | After stored at 37° C. for a month | | Initially | After stored in water at 37° C. for a month |
| | | | | Enamel | Dentin | Enamel | Dentin | | |
| 1 | 2.4 | 48 | 40 | 14.3(4.1) | 13.7(3.0) | X[3] | X[3] | 102.4(3.9) | 98.9(3.1) |
| 2 | 4.6 | 92 | 60 | 12.9(2.4) | 14.0(3.3) | X[3] | X[3] | 90.5(4.0) | 86.2(4.1) |
| 3 | — | — | 85 | 2.1(1.0) | 3.2(1.8) | 1.2(0.6) | 2.2(1.2) | 40.2(3.2) | 20.8(6.9) |
| 4 | 2.4 | 48 | 85 | 5.3(2.0) | 6.3(1.2) | 4.0(2.2) | 3.2(2.1) | 50.0(4.9) | 38.2(5.1) |
| 5 | — | — | 85 | 6.3(2.0) | 9.2(3.3) | 4.8(3.1) | 7.4(2.8) | 36.2(4.9) | 19.9(5.9) |
| 6 | 0.5 | 10 | 85 | 9.5(2.8) | 10.0(2.9) | 8.5(2.2) | 9.2(4.3) | 42.4(3.9) | 32.6(2.9) |
| 7 | 8.1 | 162 | 170 | 7.5(1.8) | 9.0(1.9) | 6.4(2.2) | 8.2(2.3) | 58.9(9.2) | 48.9(3.3) |
| 8 | — | — | 85 | 3.0(1.2) | 2.9(1.0) | 1.8(1.0) | 2.0(1.2) | 37.9(4.9) | 25.3(7.0) |
| 9 | 2 | 40 | 85 | 4.7(2.0) | 4.3(1.2) | 3.8(2.2) | 3.8(1.9) | 92.8(4.4) | 87.6(4.9) |
| 10 | 2.2 | 44 | 85 | 5.2(2.1) | 6.3(1.9) | 4.3(2.1) | 5.2(2.2) | 42.9(3.2) | 21.0(3.9) |
| 11 | 2.2 | 44 | 0 | 3.8(2.2) | 4.0(3.0) | X[3] | X[3] | 101.8(4.4) | 99.2(5.1) |
| 12 | 1 | 20 | 25 | 3.4(1.2) | 2.9(0.3) | 2.2(1.0) | 1.9(0.2) | 90.2(3.9) | 80.8(4.2) |
| 13 | 2.4 | 48 | 160 | 3.8(2.2) | 4.0(3.0) | 2.8(1.2) | 2.6(0.8) | 52.7(3.3) | 42.9(3.5) |
| 14 | 2.5 | 50 | 85 | not cured | not cured | not cured | not cured | not cured | not cured |

| Comp. Ex. No. | Luster on the surface of the cured film | | Polymerization rate of the cured film surface/% |
|---|---|---|---|
| | Initially | After stored in water at 37° C. for a month | |
| 1 | ○ | ○ | 80.2(1.0) |
| 2 | ○ | ○ | 79.2(1.1) |
| 3 | ○ | X | 50.3(2.0) |
| 4 | ○ | X | 50.6(3.3) |

TABLE 6-continued

| | | | |
|---|---|---|---|
| 5 | ○ | X | 40.2(1.2) |
| 6 | ○ | X | 52.3(1.9) |
| 7 | ○ | X | 52.7(0.7) |
| 8 | ○ | X | 47.2(2.1) |
| 9 | ○ | ○ | 79.0(1.1) |
| 10 | ○ | X | 48.9(1.8) |
| 11 | ○ | ○ | 81.2(0.7) |
| 12 | ○ | ○ | 77.6(1.2) |
| 13 | ○ | X | 54.8(1.3) |
| 14 | not cured | not cured | not cured |

[1]Amount of ions; Amounts of polyvalent metal ions eluted out into the adhesive and represented as amounts of ions/meq per a gram of the component (A).
[2]Required amount of solvent; Minimum amounts of the volatile water-soluble organic solvent (parts by mass) necessary for storing the adhesive in the form of one package.
[3]gelation In Examples 1 to 26, the components were so blended as to satisfy the constitution of the tooth surface coating material as specified by the invention. In any case, there was obtained a favorable strength of adhesion to the enamel and dentin. Even after stored in an incubator at 37° C. for a month, the tooth surface coating materials were not gelled, maintained excellent adhesion to the tooth, and could be stored favorably and stably. Further, the cured bodies exhibited favorable initial flexural strengths. The flexural strengths were not almost decreased even after left to stand in water at 37° C. for a month. Namely, the cured bodies of the tooth surface coating materials of the invention exhibited excellent water-resisting properties, high rates of polymerization in the surfaces of the cured bodies, and excellently maintained luster on the surfaces of the cured films.

In Comparative Examples 1 and 2, on the other hand, the tooth surface coating materials did not satisfy the conditions of the invention concerning the amount of blending the volatile water-soluble organic solvent (C). The cured films immediately after they were formed exhibited favorable strengths of adhesion to the tooth, water-resisting property of the cured bodies, rates of polymerization in the surfaces of the cured bodies, and excellently maintained luster on the surfaces of the cured films. However, the tooth surface coating materials underwent gelation after left to stand at 37° C. for 1 day to 5 days in the test for measuring the storage stability.

In Comparative Examples 3 and 4, the tooth surface coating material was not blended with the acidic group-containing polymerizable monomer (A1) (Comparative Example 3) or was blended with it but in an amount smaller than the amount specified by the invention (Comparative Example 4). In either case, the tooth deliming power was insufficient and, therefore, the strength of adhesion was small. Moreover, since there was no acid component or was a small amount of acid component, no polyvalent metal ion eluted out from the polyvalent metal ion-eluting filler, resulting in a great decrease in the flexural strength and water-resisting property of the cured body, in the rate of polymerization in the surface of the cured body and in the maintenance of luster on the surface of the cured film.

In Comparative Examples 5 and 6, the tooth surface coating material did not contain the polyvalent metal ion (B) (Comparative Example 5) or contained the polyvalent metal ions (B) in an amount smaller than the amount specified by the invention (Comparative Example 6). In either case, the ionic crosslinking was not formed to a sufficient degree resulting in a great decrease in the strength of adhesion to the tooth, in the water-resisting property of the cured body, in the rate of polymerization in the surface of the cured body and in the maintenance of luster on the surface of the cured body.

The tooth surface coating material of Comparative Example 7 contained the polyvalent metal ions (B) in an amount larger than the amount specified by the invention. In this case, the tooth deliming power decreased, and the volatile water-soluble organic solvent (C) had to be used in an increased amount to store the tooth surface coating material in the form of one package. After blown with the air, therefore, the effective components for forming the cured film were in short supply resulting in a great decrease in the strength of adhesion to the tooth, in the water-resisting property of the cured body, in the rate of polymerization in the surface of the cured body and in the maintenance of luster on the surface of the cured body.

In Comparative Example 8, the tooth surface coating material was not blended with water (D) and in Comparative Example 9, the tooth surface coating material was blended with water (D) in an amount smaller than the amount specified by the invention. In the former Comparative Example 8, the strength of adhesion has greatly decreased due to a decrease in the tooth deliming power. Besides, the polyvalent metal ions were not almost eluted out resulting in a great decrease in the water-resisting property of the cured body, in the rate of polymerization in the surface of the cured body and in the maintenance of luster on the surface of the cured body. In the latter Comparative Example 9, too, the tooth deliming power was small and the strength of adhesion was not sufficient.

In Comparative Example 10, the tooth surface coating material was blended with water (D) in an amount larger than the amount specified by the invention. Even after the volatile water-soluble organic solvent (C) was volatilized by blowing the air, therefore, water remained in large amounts on the applied surface resulting in a great decrease in the strength of adhesion to the tooth, in the water-resisting property of the cured body, in the rate of polymerization in the surface of the cured body and in the maintenance of luster on the surface of the cured body.

In Comparative Example 11, the tooth surface coating material was not blended with the volatile water-soluble organic solvent (D) and in Comparative Example 12, the tooth surface coating material was blended with the water-soluble organic solvent (D) in an amount smaller than the amount specified by the invention. In the former Comparative Example 11, the tooth surface coating material did not sufficiently permeate into the tooth resulting in a decrease in the initial strength of adhesion. Besides, the tooth surface coating material underwent gelation after left to stand at 37° C. for 1 day to 5 days in the test for measuring the storage stability. In the latter Comparative Example 12, too, the permeability into the tooth was insufficient, and the strength of adhesion was small.

In Comparative Example 13, the tooth surface coating material was blended with the volatile water-soluble organic solvent (D) in an amount larger than the amount specified by the invention. After blown with the air, therefore, the effective components for forming the cured film were in short supply resulting in a great decrease in the strength of adhesion to the tooth, in the water-resisting property of the cured body, in the rate of polymerization in the surface of the cured body and in the maintenance of luster on the surface of the cured body.

In Comparative Example 14, the tooth surface coating material was not blended with the photopolymerization initiator (E). In this case, the tooth surface coating material was not cured, and no cured film could be formed.

Examples 27 to 32

The tooth surface coating materials were prepared in the same manner as in Example 1 but using, as ion sources, polyvalent metal ion sources other than the polyvalent metal ion-eluting filler and changing the recipe of components as shown in Table 7, and were evaluated. The evaluated results were as shown in Table 8.

TABLE 7

| | Tooth surface protecting material composition/pts. by mass | | | | | | | | | | | | | | |
|---|---|---|---|---|---|---|---|---|---|---|---|---|---|---|---|
| | (A)[*1] | | | | (B)[*1] | | | | (C)[*1] | (D)[*1] | (E)[*1] | | Other components | | |
| Ex. | (A1) | (A2) | | | | | | | | | | | Pigments | | [*7] |
| No. | PM | BisGMA | 3G | HEMA | [*2] | [*3] | [*4] | [*5] | IPA | [*6] | CQ | DMBE | FCB | TW | Si-1 |
| 27 | 25 | 30 | 20 | 25 | 4 | | | | 85 | 15 | 1 | 1.5 | 0.01 | 0.1 | 10 |
| 28 | 25 | 30 | 20 | 25 | | 4 | | | 85 | 15 | 1 | 1.5 | 0.01 | 0.1 | 10 |
| 29 | 25 | 30 | 20 | 25 | | 7 | | | 85 | 15 | 1 | 1.5 | 0.01 | 0.1 | 10 |
| 30 | 25 | 30 | 20 | 25 | | 15 | | | 140 | 15 | 1 | 1.5 | 0.01 | 0.1 | 10 |
| 31 | 25 | 30 | 20 | 25 | | | 4 | | 85 | 15 | 1 | 1.5 | 0.01 | 0.1 | 10 |
| 32 | 25 | 30 | 20 | 25 | | | | 4 | 85 | 15 | 1 | 1.5 | 0.01 | 0.1 | 10 |

[*1]Component
[*2]Al(O-iPr)3
[*3]La(O-iPr)3
[*4]Ti(O-iPr)4
[*5]La(OH)3
[*6]Water
[*7]Inorganic filler

TABLE 8

| | | | Amount of solvent added | Strength of adhesion/MPa(S.D.) | | | | Flexural strength of the cured body/MPa (standard deviation) | |
|---|---|---|---|---|---|---|---|---|---|
| | | | | Initially | | After stored at 37° C. for a month | | | After stored in water at 37° C. for a month |
| Ex. No. | [*1] X meq | [*2] 20X | | Enamel | Dentin | Enamel | Dentin | Initially | |
| 27 | 2.4 | 48 | 85 | 19.2(1.2) | 18.5(2.2) | 18.7(3.2) | 17.5(2.9) | 96.3(5.0) | 89.7(7.0) |
| 28 | 1.5 | 30 | 85 | 17.4(2.9) | 16.8(3.3) | 15.8(1.9) | 15.1(2.8) | 87.8(9.7) | 79.6(6.1) |
| 29 | 2.7 | 54 | 85 | 21.7(3.9) | 22.6(4.4) | 19.8(3.6) | 20.4(2.1) | 112.8(9.9) | 103.7(6.9) |
| 30 | 5.7 | 114 | 140 | 18.2(4.1) | 17.3(3.7) | 17.0(2.7) | 15.9(3.4) | 92.8(3.1) | 89.5(4.7) |
| 31 | 2.3 | 46 | 85 | 20.7(3.2) | 21.6(2.4) | 19.8(5.6) | 19.4(3.1) | 102.8(4.9) | 98.7(1.9) |
| 32 | 2.5 | 50 | 85 | 20.9(4.0) | 19.2(3.7) | 18.7(1.9) | 18.4(3.3) | 95.8(4.1) | 87.9(9.2) |

| Ex. No. | Luster on the surface of the cured film | | Polymerization rate of the cured body surface/% |
|---|---|---|---|
| | Initially | After stored in water at 37° C. for a month | |
| 27 | ○ | ○ | 76.0(1.1) |
| 28 | ○ | ○ | 70.3(1.8) |
| 29 | ○ | ○ | 86.4(2.0) |
| 30 | ○ | ○ | 72.8(1.4) |
| 31 | ○ | ○ | 82.4(2.0) |
| 32 | ○ | ○ | 79.5(1.5) |

[*1]Amount of ions; Amounts of polyvalent metal ions eluted out into the adhesive and represented as amounts of ions/meq per a gram of the component (A).
[*2]Required amount of solvent; Minimum amounts of the volatile water-soluble organic solvent (parts by mass) necessary for storing the adhesive in the form of one package.

In Examples 27 to 32, the components were so blended as to satisfy the constitution of the tooth surface coating material as specified by the invention. In any case, there was obtained a favorable strength of adhesion to the enamel and dentin. Even after stored in an incubator at 37° C. for a month, the tooth surface coating materials were not gelled, maintained excellent adhesion to the tooth, and could be stored favorably and stably. Further, the cured bodies exhibited favorable initial flexural strengths. The flexural strengths did not almost decrease even after left to stand in water at 37° C. for a month. Namely, the cured bodies of the tooth surface coating materials of the invention exhibited excellent water-resisting properties, high rates of polymerization in the surfaces of the cured bodies, and excellently maintained luster on the surfaces of the cured films.

Evaluating the Abrasion and Dentinal Tubule Occlusion

Examples 33 to 64

The tooth surface coating materials were evaluated for their abrasion and dentinal tubule occlusion. The tooth surface coating materials were those shown in Tables 1, 2 and 7. The evaluated results were as shown in Tables 9, 10 and 11.

Comparative Examples 15 to 25

The tooth surface coating materials shown in Table 5 were evaluated for their abrasion and dentinal tubule occlusion. The evaluated results were as shown in Table 12.

TABLE 9

| Ex. No. | Corresponding composition | Abrasion/μm Initially *1 | *2 | *3 | Abrasion/μm After stored at 37° C. for a month *1 | *2 | *3 | Dentinal tubule blockage Initially *4 | Length of tags/μm | Dentinal tubule blockage After stored at 37° C. for a month *4 | Length of tags/μm |
|---|---|---|---|---|---|---|---|---|---|---|---|
| 33 | Example 1 | 18.7 | 16.3 | 2.4 | 20.1 | 17.5 | 2.6 | yes | 8.7(2.1) | yes | 11.0(4.4) |
| 34 | Example 2 | 19.2 | 15.2 | 4.0 | 19.7 | 15.8 | 3.9 | yes | 11.9(5.2) | yes | 10.7(5.5) |
| 35 | Example 3 | 22.3 | 17.7 | 4.6 | 23.2 | 18.9 | 4.3 | yes | 12.5(3.1) | yes | 13.7(3.1) |
| 36 | Example 4 | 21.9 | 16.2 | 5.7 | 20.6 | 15.9 | 4.7 | yes | 10.8(3.3) | yes | 11.5(4.0) |
| 37 | Example 5 | 19.9 | 16.3 | 3.6 | 20.5 | 16.8 | 3.7 | yes | 12.4(4.8) | yes | 11.9(4.2) |
| 38 | Example 6 | 20.5 | 16.8 | 3.7 | 19.9 | 16.1 | 3.8 | yes | 11.6(4.1) | yes | 10.9(4.1) |
| 39 | Example 7 | 22.1 | 17.9 | 4.2 | 19.2 | 15.6 | 3.6 | yes | 9.8(3.0) | yes | 9.3(2.9) |
| 40 | Example 8 | 19.3 | 17.1 | 2.2 | 18.9 | 16.2 | 2.7 | yes | 10.8(2.9) | yes | 9.5(3.0) |
| 41 | Example 9 | 18.9 | 17.3 | 1.6 | 21.4 | 19.5 | 1.9 | yes | 14.7(5.1) | yes | 12.9(5.1) |
| 42 | Example 10 | 21.4 | 19.6 | 1.8 | 20.6 | 18.7 | 1.9 | yes | 13.1(3.9) | yes | 14.2(4.7) |
| 43 | Example 11 | 19.9 | 17.5 | 2.4 | 21.4 | 19.1 | 2.3 | yes | 10.9(3.8) | yes | 9.2(3.1) |
| 44 | Example 12 | 20.3 | 18.4 | 1.9 | 17.9 | 15.9 | 2.0 | yes | 14.8(4.1) | yes | 10.8(3.6) |
| 45 | Example 13 | 20.4 | 18.1 | 2.3 | 18.7 | 16.2 | 2.5 | yes | 14.1(5.4) | yes | 12.4(3.7) |
| 46 | Example 14 | 19.9 | 18.2 | 1.7 | 20.5 | 18.6 | 1.9 | yes | 15.2(3.9) | yes | 13.7(3.9) |

*1: Initial thickness
*2: Thickness after abraded
*3: Abraded amount
*4: Presence of tags

TABLE 10

| Ex. No. | Corresponding composition | Abrasion/μm Initially *1 | *2 | *3 | Abrasion/μm After stored at 37° C. for a month *1 | *2 | *3 | Dentinal tubule blockage Initially *4 | Length of tags/μm | Dentinal tubule blockage After stored at 37° C. for a month *4 | Length of tags/μm |
|---|---|---|---|---|---|---|---|---|---|---|---|
| 47 | Example 15 | 22.9 | 19.2 | 3.7 | 20.2 | 16.8 | 3.4 | yes | 9.9(3.0) | yes | 10.2(4.1) |
| 48 | Example 16 | 21.5 | 18.2 | 3.3 | 19.2 | 15.9 | 3.3 | yes | 10.2(2.9) | yes | 9.9(4.5) |
| 49 | Example 17 | 19.2 | 16.4 | 2.8 | 22.4 | 19.2 | 3.2 | yes | 9.2(3.3) | yes | 10.2(3.8) |
| 50 | Example 18 | 21.2 | 17.7 | 3.5 | 18.7 | 14.9 | 3.8 | yes | 9.5(4.0) | yes | 9.7(2.2) |
| 51 | Example 19 | 20.9 | 17.5 | 3.4 | 21.6 | 18.1 | 3.5 | yes | 9.9(4.4) | yes | 10.4(4.4) |
| 52 | Example 20 | 20.4 | 17.8 | 2.6 | 19.9 | 17.2 | 2.7 | yes | 8.2(3.3) | yes | 9.1(2.5) |
| 53 | Example 21 | 19.8 | 15.1 | 4.7 | 20.5 | 15.1 | 5.4 | yes | 7.8(3.3) | yes | 8.6(4.0) |
| 54 | Example 22 | 22.9 | 19.2 | 3.7 | 19.4 | 15.9 | 3.5 | yes | 8.0(2.9) | yes | 8.9(3.3) |
| 55 | Example 23 | 22.2 | 19.9 | 2.3 | 21.3 | 18.4 | 2.9 | yes | 11.2(5.2) | yes | 10.8(4.9) |
| 56 | Example 24 | 20.8 | 19.1 | 1.7 | 17.9 | 15.8 | 2.1 | yes | 14.8(3.6) | yes | 12.9(3.8) |
| 57 | Example 25 | 19.7 | 17.8 | 1.9 | 19.2 | 17.4 | 1.8 | yes | 13.9(4.0) | yes | 14.8(4.1) |
| 58 | Example 26 | 21.6 | 19.9 | 1.7 | 21.1 | 19.4 | 1.7 | yes | 14.2(5.1) | yes | 13.7(4.5) |

*1: Initial thickness
*2: Thickness after abraded
*3: Abraded amount
*4: Presence of tags

TABLE 11

| Ex. No. | Corresponding composition | Abrasion/μm Initially *1 | *2 | *3 | Abrasion/μm After stored at 37° C. for a month *1 | *2 | *3 | Dentinal tubule blockage Initially *4 | Length of tags/μm | Dentinal tubule blockage After stored at 37° C. for a month *4 | Length of tags/μm |
|---|---|---|---|---|---|---|---|---|---|---|---|
| 59 | Example 27 | 20.7 | 18.2 | 2.5 | 17.9 | 15.2 | 2.7 | yes | 12.8(3.1) | yes | 10.2(2.6) |
| 60 | Example 28 | 20.2 | 16.5 | 3.7 | 21.1 | 17.2 | 3.9 | yes | 9.2(3.4) | yes | 8.5(2.4) |
| 61 | Example 29 | 20.2 | 18.5 | 1.7 | 18.9 | 16.8 | 2.1 | yes | 13.2(1.9) | yes | 12.2(3.4) |
| 62 | Example 30 | 21.8 | 19.1 | 2.7 | 21.1 | 18.2 | 2.9 | yes | 11.6(4.2) | yes | 10.1(3.9) |
| 63 | Example 31 | 21.2 | 19.4 | 1.8 | 19.2 | 17.1 | 2.1 | yes | 13.2(3.9) | yes | 12.5(4.4) |
| 64 | Example 32 | 19.7 | 17.8 | 1.9 | 21.2 | 19.0 | 2.2 | yes | 12.9(2.9) | yes | 10.8(2.2) |

*1: Initial thickness
*2: Thickness after abraded
*3: Abraded amount
*4: Presence of tags

TABLE 12

| Comp. Ex. No. | Corresponding composition | Abrasion/μm Initial thickness | Thickness after abraded | Abraded amount | Dentinal tubule blockage Presence of tags | Length of tags/μm |
|---|---|---|---|---|---|---|
| 15 | Comp. Ex. 3 | 19.2 | All abraded | 19.2 | no | — |
| 16 | Comp. Ex. 4 | 19.9 | All abraded | 19.9 | slightly | 1.4(0.8) |
| 17 | Comp. Ex. 5 | 21.2 | 2.2 | 19.0 | no | — |
| 18 | Comp. Ex. 6 | 20.2 | 1.9 | 18.3 | no | — |
| 19 | Comp. Ex. 7 | 19.2 | 2.4 | 16.8 | yes | 2.8(1.2) |
| 20 | Comp. Ex. 8 | 21.8 | All abraded | 21.8 | no | — |
| 21 | Comp. Ex. 9 | 18.9 | All abraded | 18.9 | no | — |
| 22 | Comp. Ex. 10 | 19.7 | 1.9 | 17.8 | no | — |
| 23 | Comp. Ex. 11 | 20.2 | 15.8 | 4.4 | no | — |
| 24 | Comp. Ex. 12 | 19.7 | 14.2 | 5.5 | no | — |
| 25 | Comp. Ex. 13 | 8.9 | All abraded | 8.9 | no | — |

* The composition of Comparative Example 23 was gelled while being stored at 37° C. for 1 day to 5 days.

In Examples 33 to 64, the components were so blended as to satisfy the constitution of the tooth surface coating material as specified by the invention. In any case, there were obtained a favorable abrasion resistance and a dentinal tubule occlusion. Even after stored in an incubator at 37° C. for a month, the tooth surface coating materials were not gelled, maintained excellent abrasion resistance and dentinal tubule occlusion, and could be stored favorably and stably.

In Comparative Examples 15 and 16, the tooth surface coating material was not blended with the acidic group-containing polymerizable monomer (A1) (Comparative Example 15) or was blended with it but in an amount smaller than the amount specified by the invention (Comparative Example 16). In former case, the tooth deliming power was insufficient and the polyvalent metal ions were not almost eluted. Therefore, no effect was obtained for improving the strength of the cured film relying on the ionic crosslinking and, besides, the cured film has all disappeared being abraded by the toothbrush. As for the dentinal tubule occlusion, further, no tag was formed. In the latter case, too, the tooth deliming power was insufficient and, therefore, the cured film has peeled off on the interface to the tooth being abraded by the toothbrush. Besides, the dentinal tubule occlusion has greatly decreased.

In Comparative Examples 17 and 18, the tooth surface coating material did not contain the polyvalent metal ion (B) (Comparative Example 17) or contained the polyvalent metal ions (B) in an amount smaller than the amount specified by the invention (Comparative Example 18). In either case, the ionic crosslinking was not formed sufficiently resulting in a great decrease in the abrasion resistance and in the dentinal tubule occlusion.

The tooth surface coating material of Comparative Example 19 contained the polyvalent metal ions (B) in an amount larger than the amount specified by the invention. In this case, the tooth deliming power decreased, and the volatile water-soluble organic solvent (C) had to be used in an increased amount to store the tooth surface coating material in the form of one package. After blown with the air, therefore, the effective components for forming the cured film were in short supply resulting in a great decrease in the abrasion resistance and in the dentinal tubule occlusion.

In Comparative Example 20, the tooth surface coating material was not blended with water (D) and in Comparative Example 21, the tooth surface coating material was blended with water (D) in an amount smaller than the amount specified by the invention. In the former case, the polyvalent metal ions were not almost eluted out and the effect of ionic crosslinking was not attained to a sufficient degree resulting in a great decrease in the abrasion resistance and in the dentinal tubule occlusion. In the latter case, the tooth deliming power was insufficient, and the cured film has peeled off on the interface to the tooth being abraded by the toothbrush.

In Comparative Example 22, the tooth surface coating material was blended with water (D) in an amount larger than the amount specified by the invention. Even after the volatile water-soluble organic solvent (C) was volatilized by blowing the air, therefore, water remained in large amounts on the applied surface resulting in a great decrease in the abrasion resistance of the cured film and in the dentinal tubule occlusion.

In Comparative Example 23, the tooth surface coating material was not blended with the volatile water-soluble organic solvent (D) and in Comparative Example 24, the tooth surface coating material was blended with the water-soluble organic solvent (D) in an amount smaller than the amount specified by the invention. In the former Comparative Example 23, the tooth surface coating material did not sufficiently permeate into the tooth resulting in a great decrease in the dentinal tubule occlusion. Besides, the tooth surface coating material underwent gelation after left to stand at 37° C. for 1 day to 5 days in the test for measuring the storage stability. In the latter Comparative Example 24, too, the permeability into the tooth was insufficient, and the dentinal tubule occlusion has greatly decreased.

In Comparative Example 25, the volatile water-soluble organic solvent (D) was blended in an amount larger than the amount specified by the invention. After blown with the air, therefore, the effective components for forming the cured film were in short supply resulting in a great decrease in the abrasion resistance and in the dentinal tubule occlusion.

The invention claimed is:

1. A one-package tooth surface coating material that is stored as one package and is used for forming an outer surface coating directly on the surface of a tooth, comprising:
    (A) a polymerizable monomer component containing not less than 5% by mass of an acidic group-containing polymerizable monomer;
    (B) polyvalent metal ions;
    (C) a volatile water-soluble organic solvent;
    (D) water; and
    (E) an effective amount of a photopolymerization initiator;
    said polyvalent metal ions (B) being present in an amount of 1.0 to 7.0 meq per gram of said polymerizable monomer component (A);
    said water-soluble organic solvent (C) being blended in an amount in a range of 30 to 150 parts by mass per 100 parts by mass of said polymerizable monomer component (A) and satisfying a condition represented by the following formula (I), $$\alpha \geqq 20 \cdot X \qquad (I)$$

wherein $\alpha$ is a blended amount of said water-soluble organic solvent (C) per 100 parts by mass of said polymerizable monomer component (A), and
    X is the amount of said polyvalent metal ions and is a number representing the amount (meq) thereof per gram of said polymerizable monomer component (A),
    and said water (D) being blended in an amount of 3 to 30 parts by mass per 100 parts by mass of said polymerizable monomer component (A).

2. The one-package tooth surface coating material according to claim 1, wherein said polyvalent metal ions (B) are present being eluted out from a polyvalent metal ion-eluting filler.

3. The one-package tooth surface coating material according to claim 1, wherein a coloring agent (F) is, further, contained.

4. The one-package tooth surface coating material according to claim 1, wherein the acidic group-containing polymerizable monomer in said polymerizable monomer component (A) is a polymerizable monomer containing a phosphoric acid group.

5. The one-package type-tooth surface coating material according to claim 2, wherein said polyvalent metal ion-eluting filler permits the polyvalent metal ions to be eluted out in an amount of 5.0 to 500 meq/g of filler when 0.1 g of said filler is added to 10 ml of an aqueous solution containing 10% by weight of maleic acid and is maintained therein at 23° C. for 24 hours.

* * * * *